US009422362B2

(12) United States Patent
Feldman et al.

(10) Patent No.: US 9,422,362 B2
(45) Date of Patent: Aug. 23, 2016

(54) TARGETED COAGULATION FACTORS AND METHOD OF USING THE SAME

(71) Applicant: Bayer HealthCare LLC, Whippany, NJ (US)

(72) Inventors: Richard Feldman, El Cerrito, CA (US); Ji-Yun Kim, Berkeley, CA (US); Haiyan Jiang, San Francisco, CA (US); Kirk Mclean, Orinda, CA (US); Junliang Pan, Moraga, CA (US); Glenn Pierce, Rancho Santa Fe, CA (US); James Wu, El Cerrito, CA (US); Xiao-Yan Zhao, Union City, CA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

(21) Appl. No.: 14/252,823

(22) Filed: Apr. 15, 2014

(65) Prior Publication Data
US 2014/0221618 A1 Aug. 7, 2014

Related U.S. Application Data

(63) Continuation of application No. 12/992,879, filed as application No. PCT/US2009/044148 on May 15, 2009, now abandoned.

(60) Provisional application No. 61/053,932, filed on May 16, 2008.

(51) Int. Cl.
C07K 14/755 (2006.01)
A61K 38/37 (2006.01)
A61K 38/48 (2006.01)

(52) U.S. Cl.
CPC ............... C07K 14/755 (2013.01); A61K 38/37 (2013.01); A61K 38/4846 (2013.01)

(58) Field of Classification Search
CPC .................................................. C07K 14/755
See application file for complete search history.

(56) References Cited

U.S. PATENT DOCUMENTS 7,985,839 B2    7/2011  Turecek et al.
2003/0087826 A1* 5/2003  Church et al. .................. 514/12

FOREIGN PATENT DOCUMENTS

| JP | 2001504813 A | 4/1998 |
| JP | 2001523648 A | 5/1999 |
| WO | 9409034 A1 | 4/1994 |
| WO | 9817319 A2 | 4/1998 |
| WO | 9925383 A1 | 5/1999 |
| WO | 02102850 A2 | 12/2002 |
| WO | 2006053299 A2 | 5/2006 |
| WO | 2006078914 A1 | 7/2006 |

OTHER PUBLICATIONS

Stoll (Arterioscler Thromb Vasc Biol. May 2007;27(5):1206-12. Epub Feb. 22, 2007).*
Chinese Office action received in Patent Application No. 200980126328.5 mailed May 24, 2013.
Chen et al., "Fusion proteins comprising annexin V and Kunitz protease inhibitors are highly potent thrombogenic site-directed anticoagulants," Blood, 2005, 105(10):3902-3909.
Dong et al., "P-selectin-targeting of the Fibrin Selective Thrombolytic Desmodus Rotundus Salivary Plasminogen Activator α1," Thromb Haemost. vol. 92, pp. 956-965, 2004.
Stoll et al., "Targeting ligand-induced binding sites on GPIIb/IIIa via single-chain antibody allows effective anticoagulation without bleeding time prolongation," Arterioscler Thromb Vasc. Biol. 2007; 27(5): 1206-1212.
Parise et al., "Platelet Membrane Glycoprotein IIb-IIIa Complex Incorporated into Phospholipid Vesicles," J Biological Chemistry, 1vol. 260, No. 3, pp. 1750-1756, 985.
International Search Report and Written Opinion of International Application No. PCT/US09/044148 (BH-002/PCT) mailed Oct. 22, 2009.
International Preliminary Report on Patentability of International Application No. PCT /US09/044148 (BH-002/PCT) mailed Nov. 17, 2010.
Bovenschen et al., "The B domain of coagulation factor VIII interacts with the asialoglycoprotein receptor". Journal of Thrombosis and Haemostasis, vol. 3, pp. 1257-1265 (2005).
Kane et al., "Blood Coagulation Factors V and VIII: Structural and Functional Similarities and Their Relationship to Hemorrhagic and Thrombotic Disorder". Blood, vol. 71, No. 3, pp. 539-555 (1988).
Gruppo, et al., Comparative effectiveness of full-length and B-domain deleted factor VIII for prophylaxis—a meta-analysis, Haemophila 9:251-260, 2003.
Saenko, et al, Haemophilia A: effects of inhibitory Antibodies on factor VIII functional interactions and approaches to prevent their action, Haemophilia 8:1-11, 2002.
Shi, et al., Factor VIII ectopically targetted to platelets is therapeutic in hemophilia A with high-titer inhibitory antibodies; J. Clin. Invest. 116(7): 1974-1982, 2006.
Thompson, Structure and Function of the Factor VIII gene and Protein, Semin. Thromb. Hemost. 29:11-22, 2003.
Schwarz, et al, Conformation-Specific Blockade of the Integrin GPIIb/IIIa, A Novel Antiplatelet Strategy That Selectively Targets Activated Platelets, Circ. Res. 99(I):25-33, 2006.

(Continued)

Primary Examiner — Amber D Steele
(74) Attorney, Agent, or Firm — Bayer Healthcare LLC

(57) ABSTRACT

Targeted coagulation factors comprising a coagulation factor linked with at least one domain that specifically binds to a membrane protein on a blood cell is provided. The disclosed targeted coagulation factors increase the efficiency of coagulation factors and prolong their duration of action and thus, are an improvement for the treatment of hematological diseases such as hemophilia A.

15 Claims, 7 Drawing Sheets

(56) References Cited

OTHER PUBLICATIONS

Jacobin, et al., Improving selection of αIIbβ3-binding phage antibodies with increased reactivity derived from immunized donors, Clin. Immunol. 108(3): 199-210, 2003.

Christopoulos, et al., Flow cytometric observations on the in vivo use of FAB fragments of a chimaeric monoclonal antibody to platelet glycoprotein IIb-IIIa, Blood Coagul. Fibrinolysis 4(5)129-37, 1993.

Chung, et al., Integrin αIIbB3-specific synthetic human monoclonal antibodies and HCDR3 peptides that potently inhibit platelet aggregation1, FASEB J. 18(2):361-363, 2004.

Hu, P. et al., "Comparison of Three Different Targeted Tissue Factor Fusion Proteins for Inducing Tumor Vessle Thrombosis," Cancer Res., (2003), vol. 63, pp. 5046-5053.

Japanese office action for Japanese Patent Application No. 2011-509738 mailed Nov. 12, 2013.

* cited by examiner

TARGETED COAGULATION FACTORS AND METHOD OF USING THE SAME

This application claims benefit of U.S. Non-provisional application Ser. No. 12/992,879, filed Nov. 15, 2010 and published as U.S. Publication No. 2011/0077202, which claims benefit to International Publication No. WO 2009/140598, filed May 15, 2009, which claims benefit to U.S. Provisional Application Ser. No. 61/053,932; filed on May 16, 2008, the disclosures of which are incorporated herein by reference in their entireties.

INCORPORATION OF SEQUENCE LISTING

A paper copy of the Sequence Listing and a computer readable form of the sequence listing containing the file named "MSB-7328_ST25.txt" which is 67,501 bytes in size (measured in MICROSOFT WINDOWS® EXPLORER) are provided herein and are herein incorporated by reference. This Sequence Listing consists of SEQ ID NOs:1-7.

FIELD OF THE INVENTION

The invention relates to targeted coagulation factors having increased efficacy. The invention further provides methods of treating patients suffering from a coagulation factor deficiency disorder by selectively targeting coagulation factors to their biological sites of action, such as by targeting Factor VIII (FVIII) to red blood cells and platelets. Pharmaceutical compositions comprising the targeted coagulation factors according to the invention are also provided.

BACKGROUND OF THE INVENTION

The effectiveness of biological drugs is often limited by their duration of action in patients, particularly when the disease requires constant modulation by the drug. Consequently, enhancement of pharmacokinetic properties is often more critical to the success of a therapeutic agent in the clinic than is optimization of the drug's potency. One approach to protect drugs from various mechanism of clearance so to prolong the half-life is to add targeting domains that promote drug binding to long-lived proteins in circulation such as matrix proteins, or to the surface of cells, such as blood cells or endothelial cells. For example, localization of therapeutic peptides or proteins to blood cell surfaces has been shown to prolong their circulation half-life by preventing normal clearance mechanisms (Chen, et al, Blood 105(10):3902-3909, 2005). A wide variety of molecules may be used as the targeting domain.

In another instance, when the Kunitz-type protease inhibitor (KPI) domain of tick anticoagulant protein was linked with an anionic phospholipid, phosphatidyl-L-serine (PS) binding protein, annexin V (ANV), the fusion protein (ANV-KPI) was shown to be more active and possess higher in vivo antithrombotic activities than the non-fusion counterpart (Chen, et al., 2005). Because ANV has strong affinities for PS and phosphatidylethanolamine (PE), it is hypothesized that the fusion protein ANV-KPI can be specifically targeted to the PS/PE-rich anionic membrane-associated coagulation enzyme complexes present at sites of thrombogenesis. Similarly, Dong, et al, reported fusing the fibrin-selective Desmodus rotundus salivary PA α1 (dsPA α1) to a urokinase (uPA)/anti-P-selectin antibody (HuSZ51) to produce a fusion protein that is fully functional with similar antithrombotic activities as the non-fusion counterpart in in vitro assays. Furthermore, the fusion protein HuSZ51-dsPA α1 was shown to bind to thrombin-activated human and dog platelets (Dong, et al., Thromb. Haemost. 92:956-965, 2004).

Other efforts have been made in targeting anticoagulants to prevent clots and to reduce mortality associated with thrombotic diseases (see, e.g., WO 94/09034). A more recent development is demonstrated by Stoll, et al., (Arterioscler. Thromb. Vasc. Biol. 27:1206-1212, 2007), in which a Factor Xa (FXa) inhibitor, tick anticoagulant peptide (TAP), was targeted to ligand-induced binding sites (LIBS) on GPIIb/IIIa, a glycoprotein abundantly expressed on the platelet surface, via an anti-LIBS single-chain antibody ($scFv_{anti-LIBS}$). The fusion protein $scFv_{anti-LIBS}$-TAP was shown to possess an effective anticoagulation activity even at low doses at which the non-targeted counterpart failed.

The aforementioned targeted anticoagulants were fusion proteins designed to target specific cells. According to Stoll, et al., the targeted anticoagulant should be a small molecule with a highly potent coagulation inhibition activity that is retained while fused to an antibody. The release of the anticoagulant from the fusion proteins in its targeted sites was not discussed.

The present invention focuses on targeting therapeutic proteins for the treatment of hematological diseases such as hemophilia. For example, current treatment of hemophilia A patients with FVIII concentrates or recombinant FVIII is limited by the high cost of these factors and their relatively short duration of action. Hemophilia A patients are currently treated by intravenous administration of FVIII on demand or as a prophylactic therapy administered several times a week. For prophylactic treatment, FVIII is administered three times a week. Unfortunately, this frequency is cost prohibitive for many patients. Because of its short half-life in man, FVIII must be administered frequently. Despite its large size of greater than 300 kD for the full-length protein, FVIII has a half-life in humans of only about 11-18 (average 14) hours (Gruppo, et al., Haemophila 9:251-260, 2003). For those who can afford the frequent dosaging recommended, it is nevertheless very inconvenient to frequently intravenously inject the protein. It would be more convenient for the patients if a FVIII product could be developed that had a longer half-life and therefore required less frequent administration. Furthermore, the cost of treatment could be reduced if the half-life were increased because fewer dosages may then be required. It is therefore desirable to have more efficient forms of FVIII that can lower the effective dose or have a prolonged duration of action to significantly improve treatment options for hemophiliacs.

Also, a sustained plasma concentration of targeted FVIII may reduce the extent of adverse side effects by reducing the trough to peak levels of FVIII, thus eliminating the need to introduce super-physiological levels of protein at early timepoints. Therefore, it is desirable to have forms of FVIII that have sustained duration and a longer half-life than current marketed forms.

An additional disadvantage to the current therapy is that about 25-30% of patients develop antibodies that inhibit FVIII activity (Saenko, et al, Haemophilia 8:1-11, 2002). Antibody development prevents the use of FVIII as a replacement therapy, forcing this group of patients to seek an even more expensive treatment with high-dose recombinant Factor VIIa (FVIIa) and immune tolerance therapy. A less immunogenic FVIII replacement product is therefore desirable.

One approach in improving the treatment for hemophiliacs involves gene therapy. Ectopically targeting FVIII to platelets by directing FVIII expression in platelets can have therapeutic effects in the treatment of hemophilia A (Shi, et al., J. Clin. Invest. 116(7): 1974-1982, 2006).

It is an object of the invention to provide targeted coagulation factors that have prolonged duration of action, greater efficacy, fewer side effects, and less immunogenicity compared to the untargeted protein.

Another object of the invention is to reduce side effects associated with therapeutic protein administration by having the protein targeted to the specific site of desired action and thereby reducing the exposure of the protein to other potential biologically active sites that may result in undesired side effects.

A further object of the present invention is to obtain further advantages by designing targeted therapeutic coagulation factors in which the therapeutic protein is released from the targeting domain in the immediate vicinity of its site of action in vivo. A high local concentration of the non-fusion, activated proteins may be achieved. Thus, the therapeutic efficacy of the proteins is enhanced.

SUMMARY OF THE INVENTION

The targeted coagulation factors according to the present invention comprise a coagulation factor linked with at least one domain that specifically binds to a membrane protein on a blood cell. A pharmaceutical composition comprising the newly disclosed targeted coagulation factors and a method for treating hematological diseases using the targeted coagulation factors is also provided. The present invention further provides a method for targeting a coagulation factor to the surface of a blood cell by using the newly disclosed targeted coagulation factors to increase the efficiency of treating hematological disease with coagulation factors.

DESCRIPTION OF THE INVENTION

Figure 1:
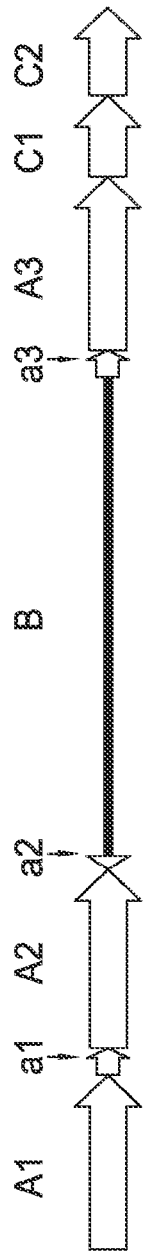
FIG. 1: Schematic drawings of full-length FVIII ("Full Length FVIII") and B-domain deleted FVIII ("FVIII-BDD-TD") in which a targeting domain ("TD") is inserted into the B-domain and most of the B-domain is removed.
Figure 1:
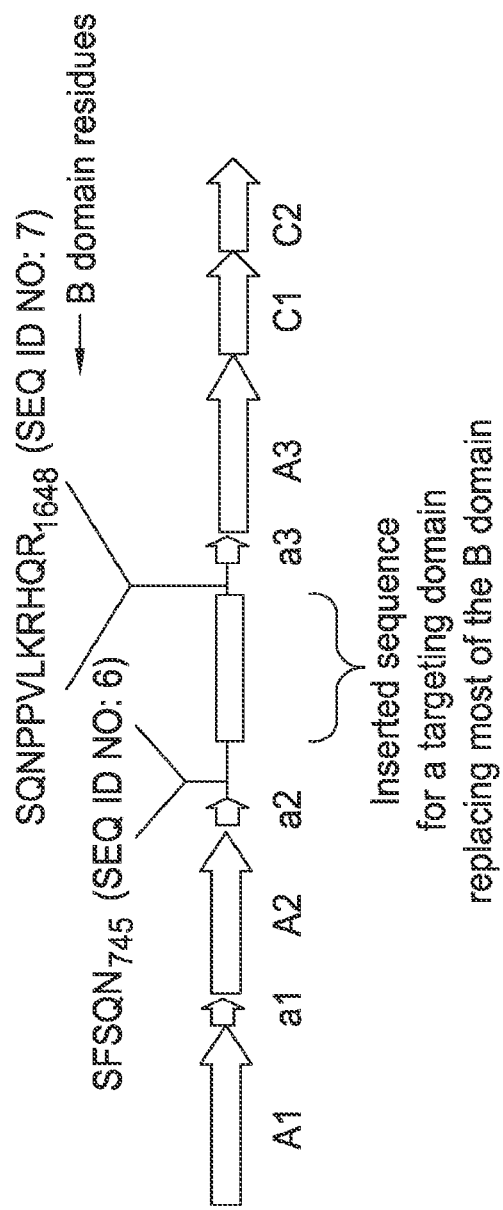

The present invention is directed to targeting a coagulation factor to its site or sites of action, such as to blood cells. In one embodiment, a targeted coagulation factor is provided that is specifically targeted to a blood cell through linking the factor to at least one domain that binds to a membrane protein on the blood cell. The domain for targeting the coagulation factor to the blood cell may be, without limitation, an antibody fragment, an antibody, a peptide, a receptor ligand, a carbohydrate, or a small molecule that has a high affinity to a membrane protein on the surface of the blood cell. The blood cell, for example, is a red blood cell or a platelet.

As used herein, "coagulation factor" refers to a protein that is involved in the coagulation cascade and has predominantly procoagulant activity. Coagulation factors are well known in the art and include without limitation coagulation factors I, II, V, VI, VII, VIII, IX, X, XI, XII, and XIII, and protein S. The coagulation factors may be concentrated from plasma or may be recombinantly produced. If recombinantly produced, the coagulation factors may have an amino acid structure that varies from the natural structure as long as sufficient procoagulant activity is maintained such that the variant is therapeutically useful. In one embodiment, the coagulation factor is a functional FVIII polypeptide, such as without limitation a FVIII concentrate from plasma or recombinantly produced FVIII, or Factor IX (FIX).

"Functional FVIII polypeptide" as used herein denotes a functional polypeptide or combination of polypeptides that are capable, in vivo or in vitro, of correcting human FVIII deficiencies, characterized, for example, by hemophilia A. FVIII has multiple degradation or processed forms in the natural state. These are proteolytically derived from a precursor, one chain protein. A functional FVIII polypeptide includes such single chain protein and also provides for these various degradation products that have the biological activity of correcting human FVIII deficiencies. Allelic variations likely exist. The functional FVIII polypeptides include all such allelic variations, glycosylated versions, modifications and fragments resulting in derivatives of FVIII so long as they contain the functional segment of human FVIII and the essential, characteristic human FVIII functional activity. Those derivatives of FVIII possessing the requisite functional activity can readily be identified by straightforward in vitro tests described herein. Furthermore, functional FVIII polypeptide is capable of catalyzing the conversion of Factor X (FX) to FXa in the presence of Factor IXa (FIXa), calcium, and phospholipid, as well as correcting the coagulation defect in plasma derived from hemophilia A affected individuals. From the published sequence of the human FVIII amino acid sequence and the published information on its functional regions, the fragments that can be derived via restriction enzyme cutting of the DNA or proteolytic or other degradation of human FVIII protein will be apparent to those skilled in the art. Specifically included within functional FVIII polypeptides without limitation is full-length human FVIII (e.g., SEQ ID NO: 1 and SEQ ID NO: 2) and B-domain deleted factor VIII (e.g., SEQ ID NO: 3 and SEQ ID NO: 4) and having the amino acid sequences as disclosed in WO 2006/053299.

"Procoagulant activity" of FVIII refers to the activity of FVIII in the coagulation cascade. FVIII itself does not cause coagulation, but plays an essential role in the coagulation cascade. The role of FVIII in coagulation is to be activated to FVIIIa, which is a catalytic cofactor for intrinsic FX activation (Thompson, Semin. Thromb. Hemost. 29:11-22, 2003). FVIII is proteolytically activated by thrombin or FXa, which dissociates it from von Willebrand factor (vWf) and activates its procoagulant function in the cascade. In its active form, FVIIIa functions as a cofactor for the FX activation enzyme complex in the intrinsic pathway of blood coagulation, and it is decreased or nonfunctional in patients with hemophilia A.

"FIX" means coagulation factor IX, which is also known as human clotting factor IX, or plasma thromboplastin component.

As used herein, the term "targeted coagulation factor" refers to a coagulation factor that is coupled with at least one domain that specifically binds to a membrane protein on a blood cell. The targeted coagulation factor should bind potently to the blood cells, for example, with a half maximal binding <10 nM. Binding should be specific to the targeted blood cells, for example, through binding to membrane proteins selectively expressed on the targeted cell. "Domain" or "targeting domain" as used herein refers to a moiety that has a high affinity for membrane proteins on target cells. Domains suitable for the present invention include, but are not limited to, antibodies, antibody fragments, such as single chain antibodies (svFv) or FAB fragments, antibody mimetics, and peptides or small molecules with high affinity for membrane proteins on the surface of the blood cells. In one aspect, a single chain antibody fragment or a peptide is used because its coding sequence can be linked with the FVIII coding sequence and a fusion protein can be produced using recombinant technology.

The coagulation factor can be coupled with the domain either chemically or by recombinant expression of a fusion protein. Chemical linkage can be achieved by linking together chemical moieties present on the coagulation factor and the targeting domain, including chemical linkages using moieties such as amino, carboxyl, sulfydryl, hydroxyl groups, and carbohydrate groups. A variety of homo- and hetero-bifunctional linkers can be used that have groups that are activated, or can be activated to link to attach these moieties. Some useful reactive groups on linker molecules include maleimides, N-hydroxy-succinamic esters and hyrazides. Many different spacers of different chemical composition and length can be used for separating these reactive groups including, for example, polyethylene glycol (PEG), aliphatic groups, alkylene groups, cycloalkylene groups, fused or linked aryl groups, peptides and/or peptidyl mimetics of one to 20 amino acids or amino acid analogs in length. For example, the domain may be linked with the coagulation factor in such a way that in vivo a functional form of the coagulation factor would be released from its targeted domain or the release occurs at or near the site of biological activity of the coagulation factor in the body.

Accordingly, in one embodiment of the invention, a targeted coagulation factor is provided wherein the linkage attaching the coagulation factor to the domain for targeting the coagulation factor to the blood cell can be cleaved or degraded thereby releasing the coagulation factor from the conjugate.

The release of the coagulation factors from their conjugate form (i.e., from the targeted coagulation factor) can be achieved by linking the targeting domain to a site on the coagulation factor that is removed during its activation process, or by using a linker that degrades in a controlled manner by enzymes in the blood. For example, sugar polymers or peptides can be used that are susceptible to general blood proteases or hydrolases. A variety of such technologies is known in the art and has been used to make pro-drugs. The linker could be further engineered to be cleaved specifically at sites where the coagulation factors are most needed, such as sites of inflammation or blood coagulation triggered through trauma. For example, the linker may be susceptible to specific proteases produced only at the desired site of action, such as proteases released by the inflammation process or generated by the blood coagulation cascade. This selective release of the therapeutic protein may lower the potential for side effects and increase the efficiency of the protein at its site of action.

A variety of membrane proteins on blood cells can be targeted according to the present invention. To specifically and efficiently target a coagulation factor to a blood cell, however, it is preferable that the targeted membrane protein is present abundantly on the blood cell surface. For example, the glycoprotein GPIIb/IIIa is found to be one of the most abundantly expressed molecules on the platelet surface.

Accordingly, in one embodiment, the coagulation factor is targeted to a platelet through a domain that binds specifically to a platelet membrane protein such as the glycoprotein GPIIb/IIIa. Examples of such domains to target the coagulation factor to GPIIb/IIIa include, but are not limited to, RGD containing peptides and mimetics (linear peptides, snake venom peptides, and cyclic peptides) such as integrilin containing the RGD mimetic sequence, homo-arginine, glycine aspartic acid), non-peptide RGD mimetics, and anti-GPIIb/IIIa antibodies. If an antibody is used as the targeting domain, a single chain fragment of the antibody, such as svFv or FAB fragment, can be used.

Targeting FVIII and FIX

Targeting FVIII and FIX to the surface of blood cells, such as platelets or red blood cells, may serve to slow the clearance of these coagulation factors. Targeting FVIII to the surface of platelet cells is of particular interest. FVIII is a critical cofactor in the FIX-mediated activation of FX, which takes place predominantly on the surface of activated platelet cells that accumulate at clot sites. Activation of platelets triggers binding of these coagulation factors to its surface to form a complex that facilitates FXa generation. Platelets have an average lifespan in circulation of about 9 days. In contrast, FVIII in plasma (largely bound to von Willebrand's factor) displays a half-life of about 14 hours. Thus, binding of FVIII to platelets has the potential to greatly extend the circulation time of the molecule. Targeting FVIII to the surface of platelet cells via a targeting domain according to the present invention increases the efficiency of FVIII action and is anticipated to prolong the half-life of FVIII.

In addition to GPIIb/IIIa, other proteins on platelets could serve as receptors for targeted FVIII, such as GP1a and Anexin V. The glycoprotein GPIIb/IIIa is preferred because it is one of the most abundantly expressed molecules on the platelet surface. The concentration of GPIIb/IIIa in blood is estimated to be about 75 nM based on its surface density on platelets. This represents a 100-fold excess over the maximum concentration of FVIII achieved after therapeutic application of the FVIII ($C_{max}$ about 0.7 nM). Therefore, targeting of FVIII to platelets would occupy roughly 1% or less of available GPIIb/IIIa sites on platelets. This low level of occupancy would not be expected to alter platelet function, which requires a much larger fraction (i.e., >50-60%) of GPIIb/IIIa molecules to be blocked. The high concentration of GPIIb/IIIa would also drive the equilibrium binding of targeted FVIII to the platelet surface.

Without restricting the invention in any way, it is believed that targeting FVIII to GPIIb/IIIa may also have the benefit that some of the coagulation factors may be internalized through endocytosis and recycling of GPIIb/IIIa through the open intracanicular system of platelets. This FVIII can end up in alpha granules and be re-released upon platelet activation, providing a source of FVIII when it is needed for coagulation. Bound or internalized FVIII targeted to platelets may be protected from inhibitors (e.g., FVIII antibodies) that are present in many patients. Thus, targeted FVIII may offer a treatment option for this important group of patients.

For targeted FVIII to promote coagulation, the molecule must be capable of being processed to a functional form (FVIIIa), and be released from its GPIIb/IIIa binding site. In one embodiment, this is achieved by linking the GPIIb/IIIa targeting domain to the B-domain of FVIII. The B-domain is removed in a pro-coagulant environment by thrombin or FXa mediated proteolysis, producing the mature FVIIIa molecule. Thus, upon activation, FVIIIa will be released from GPIIb/IIIa and be available for formation of the FX activation complex.

The linkage between FVIII and the targeting domain can be achieved by covalently binding the targeting domain to reactive groups on FVIII, including amino, sulfhydryl, carboxyl groups and carbonyl groups using cross-linking approaches described herein. Targeting domains can also be coupled to carbohydrate present mostly on the B-domain of the FVIII molecule. For example, mild oxidation of FVIII with periodate produces aldehydes on carbohydrate chains, which can then be reacted with amines or hyrazides, followed optionally by reduction to form more stable linkages.

Free cysteine can be selectively generated on the B-domain of recombinant FVIII through mild reduction with Tris(2-carboxyethyl)phosphine (TCEP), allowing specific linking of the B-domain with a targeting domain that reacts with a free cysteine, such as a domain containing a thiol, triflate, tresylate, aziridine, oxirane, S-pyridyl, or maleimide moiety. Furthermore, FVIII can be modified to replace an amino acid residue with cysteine to provide a specific location for attachment to a targeting domain. If a B-domain deleted FVIII is used, a variety of cysteine muteins of B-domain deleted FVIII, such as those disclosed in WO 2006/053299, can be used to link FVIII with a targeting domain through chemical binding at a surface cysteine residue. Examples of amino acid residues that may be modified to replace an amino acid residue with cysteine include, but are not limited to, 81, 129, 377, 378, 468, 487, 491, 504, 556, 570, 1648, 1795, 1796, 1803, 1804, 1808, 1810, 1864, 1911, 2091, 2118, and 2284 (the amino acid residue is designated by its position in the sequence of full-length FVIII).

The coagulation factor may also be coupled to the targeting domain using recombinant technology. Host cells may be transfected with a vector comprising a fusion protein of FVIII and the targeting domain. In one embodiment, the targeting domain may be inserted into the B-domain of FVIII and most of the B-domain is deleted with only portions of the B-domain left at the carboxy and amino terminals to allow for the biological processing of the B-domain to delete it from the full-length molecule. As illustrated in FIG. 1, the remaining portions of the B-domain are specified that allow for biological processing and removal of the B-domain under physiological conditions.

The host cell line may be any cell known to those skilled in the art as useful for producing a coagulation factor such as, without limitation, for FVIII CHO cells, HEK cells, BHK cells, and HKB11 cells (a hybrid of a human embryonic kidney cell line, HEK293 and a human Burkitt B cell lymphoma line, 2B8).

A number of domains can be linked chemically to FVIII, or recombinantly expressed with FVIII, to target FVIII to GPIIb/IIIa on the surface of platelets. Examples of such domains include, but are not limited to, antibodies against GPIIb/IIIa, RGD peptides, peptide mimetics, or small molecule mimetics targeting GPIIb/IIIa. Antibodies, such as single chain antibodies (svFv) or FAB fragments targeting GPIIb/IIIa, are particularly useful as targeting domains.

It has been shown that the B-domain of FVIII can be removed without loss of FVIII function. Additionally, it has been also shown that various B-domain truncated forms of FVIII and B-domain fusions with other protein domains can yield functionally active FVIII. In one aspect, the invention involves targeting domains that can be engineered to insert into, replace, or partially replace the B-domain of FVIII without blocking the normal processing of the molecule to yield active FVIII. For example, using recombinant DNA technology, a FVIII molecule can be produced in which single chain antibody fragments are fused to the C-terminus of the B-domain of FVIII. Alternatively, svFv fragments can also be used to replace the whole or a part of the B-domain of FVIII. This can be achieved through insertion of the DNA sequence encoding the svFv fragments, in frame, after the B-domain coding sequence, or replacing some or all of the B-domain coding sequence. This strategy will preserve thrombin cleavage sites required for normal proteolyic activation of FVIII. A variety of antibodies against GPIIb/IIIa which localize efficiently to platelets are known (see, e.g., Schwarz, et al, Circ. Res. 99(1):25-33, 2006; Jacobin, et al., Clin. Immunol. 108 (3): 199-210, 2003; Christopoulos, et al., Blood Coagul. Fibrinolysis 4(5):729-37, 1993; and Chung, et al., FASEB J. 18(2):361-363, 2004).

Likewise, RGD or RGD mimetic containing peptides are also useful ligands for targeting FVIII since many of such peptides have been described to have high binding affinity to GPIIb/IIIa. These include linear peptides, snake venom peptides, and cyclic peptides. Non-peptide RGD mimetics could also be used. Similar to the antibody fragments, RGD peptides can be chemically coupled to FVIII. Alternatively, RGD sequences can be inserted into the B-domain coding sequence or used to replace, in whole or in part, the B-domain coding sequence of FVIII and expressed using recombinant DNA technology.

A targeted FIX can be prepared using a similar procedure. For example, targeting domains can be linked to an activation domain of a FIX molecule (amino acid residues 191-226 or 145-180, depending on preferences, that is, +/− signal sequence), which is proteolytically removed in the activation of FIX to FIXa. The domain can be linked chemically using cross-linkers reactive with amino acid side chain groups such as sulfhydryls, amines, and carboxyl groups in the activation domain, or linked through carbohydrate chains, as was discussed above for FVIII. A fusion molecule can also be made using recombinant technology where an amino acid sequence of a targeting domain is inserted into the FIX activation peptide, or replacing parts of the activation peptide sequence. The inserted targeting domain sequences can code for a single chain antibody, or other platelet binding peptide sequence, such as an RGD binding peptide.

Pharmaceutical Compositions and Uses

The invention also concerns pharmaceutical compositions comprising therapeutically effective amounts of the targeted coagulation factors of the invention and a pharmaceutically acceptable excipient or carrier. "Pharmaceutically acceptable excipient or carrier" is a substance that may be added to the active ingredient to help formulate or stabilize the preparation and causes no significant adverse toxicological effects to the patient. Examples of such excipients or carriers are well known to those skilled in the art and include water, sugars such as maltose or sucrose, albumin, salts, etc. Other excipients or carriers are described, for example, in Remington's Pharmaceutical Sciences (Mack Publishing Co., Easton, Pa., $20^{th}$ edition, 2000). Such compositions will contain an effective amount of the targeted coagulation factors together with a suitable amount of excipients or carriers to prepare pharmaceutically acceptable compositions suitable for effective administration to a patient in need thereof.

For example, the conjugate may be parenterally administered to subjects suffering from hemophilia A at a dosage that may vary with the severity of the bleeding episode. The average doses administered intravenously is in the range of 40 units per kilogram for pre-operative indications, 15 to 20 units per kilogram for minor hemorrhaging, and 20 to 40 units per kilogram administered over an 8-hours period for a maintenance dose.

In one embodiment, the present invention concerns a method for treating hematological diseases comprising administering an therapeutically effective amount of the aforementioned targeted coagulation factor to a patient in need thereof.

As used herein, "therapeutically effective amount" means an amount of a targeted coagulation factor that is need to provide a desired level of the targeted factor (or corresponding unconjugated factor released from the targeted form) in the bloodstream or in the target tissue. The precise amount will depend upon numerous factors, including, but not limited to the components and physical characteristics of the therapeutic composition, intended patient population, individual patient considerations, and the like, and can readily be determined by one skilled in the art.

As used herein, "patient" refers to human or animal individuals receiving medical care and/or treatment.

The polypeptides, materials, compositions, and methods described herein are intended to be representative examples of the invention, and it will be understood that the scope of the invention is not limited by the scope of the examples. Those skilled in the art will recognize that the invention may be practiced with variations on the disclosed polypeptides, materials, compositions and methods, and such variations are regarded as within the ambit of the invention.

The following examples are presented to illustrate the invention described herein, but should not be construed as limiting the scope of the invention in any way.

EXAMPLES

In order that this invention may be better understood, the following examples are set forth. These examples are for the purpose of illustration only, and are not to be construed as limiting the scope of the invention in any manner. All publications mentioned herein are incorporated by reference in their entirety.

Example 1

Modified RGD Peptides with High Affinity for GPIIb/IIIa Binding

Figure 2:
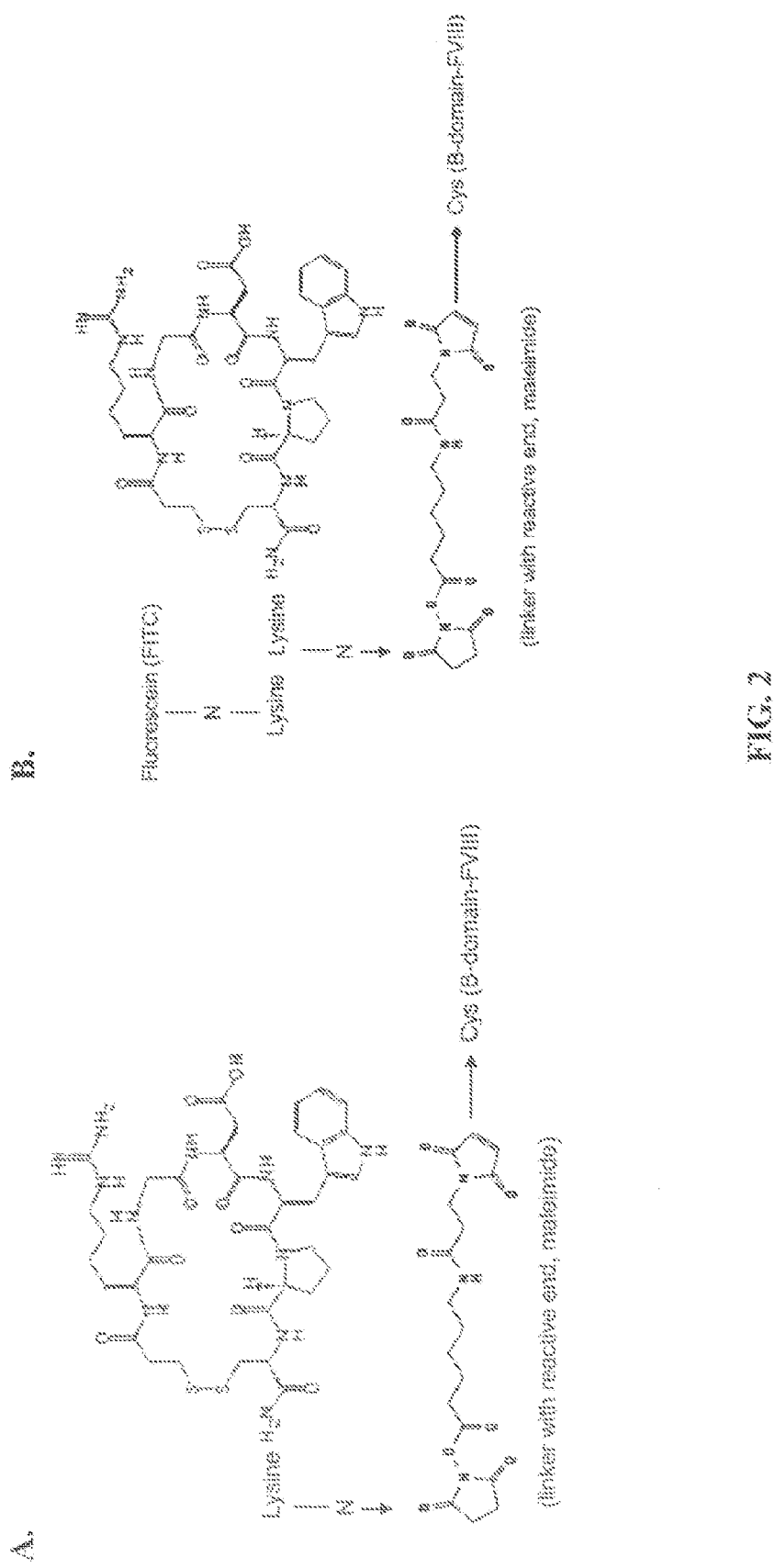
FIG. 2: Structures of modified cyclic peptide integrilin, "BHRF-1" (A) and "BHRF-3" (B), for linking to FVIII through the B-domain cysteine.
Figure 3:
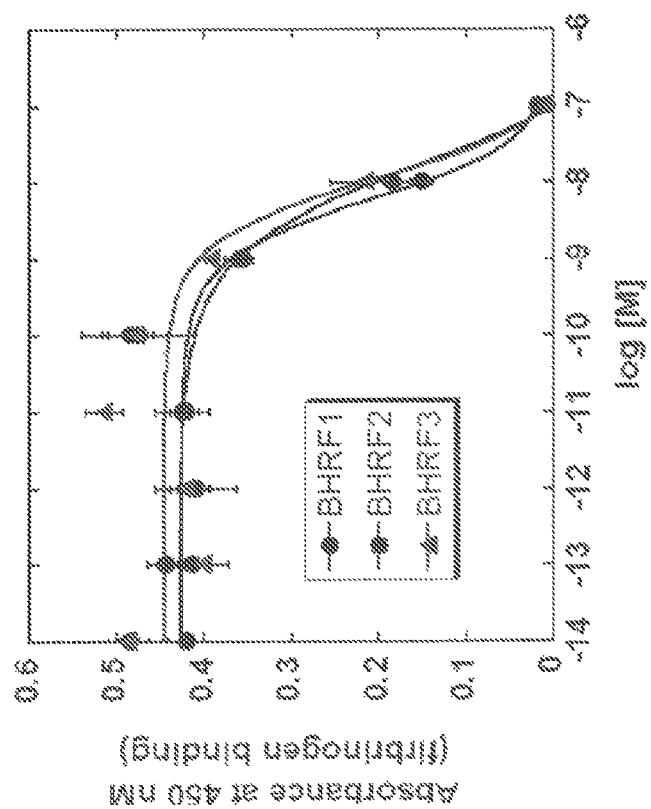
FIG. 3: Binding affinity of BHRF-1 and BFRH-3 to immobilized GPIIa/IIIb.
Figure 4:
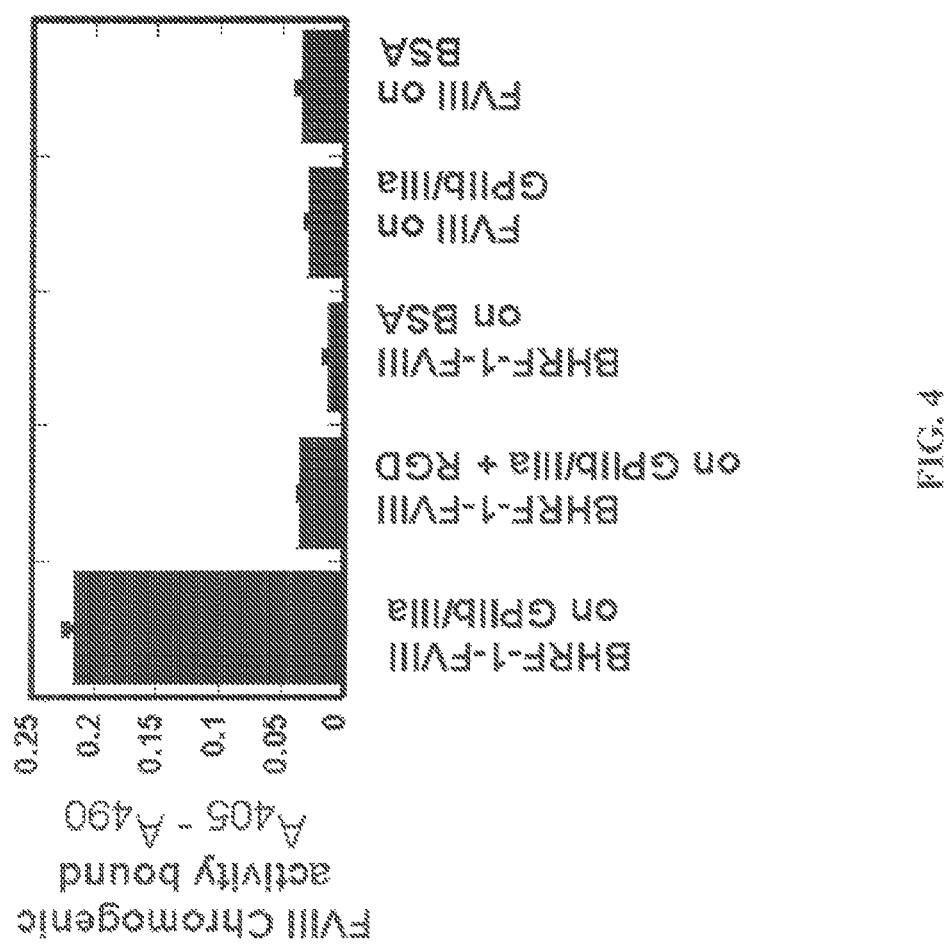
FIG. 4: BHRF-1-FVIII binding assay to immobilized GPIIa/IIIb.
Figure 5:
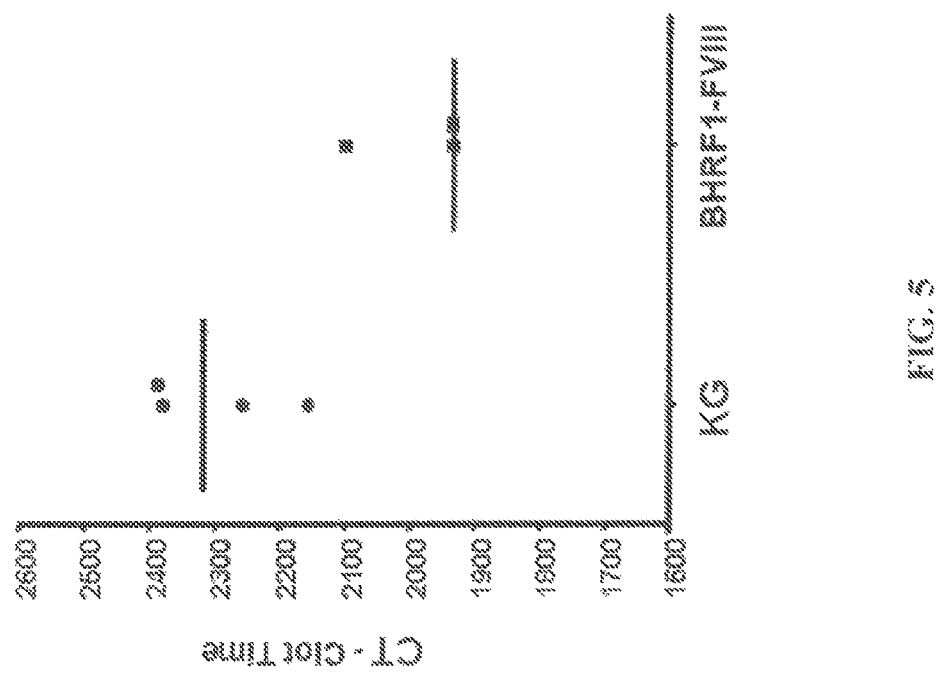
FIG. 5: In vitro clotting activity of BHRF-1-FVIII as compared with FVIII.

Cyclic peptides have been described to bind potently and selectively to GPIIb/IIIa. One such peptide, integrilin, was used as a targeting domain to link with FVIII as it has been shown that integrilin can selectively bind to GPIIb/IIIa. Integrilin was modified by adding a short PEG linker ending in a maleimide moiety that can selectively couple to free cysteine residues in proteins. The modified integrilin is termed BHRF-I with the linker only (FIG. 2A), and BHRF-3 with the linker and a fluorescein (FITC) (FIG. 2B). As shown in FIG. 3, the modified integrilins retain affinity for GPIIb/IIIa as they potently blocked fibrinogen (Fbn) binding to immobilized GPIIa/IIIb.

Peptide binding to GPIIb-IIIa was measured using a solid phase binding assay in which competition of fibrinogen binding by testing compounds is measured. The assay was performed as follows. Purified GPIIb-IIIa (Innovative Research, Novi, Mich.) was coated onto 96-well Immulon-B plates at 0.mL/well×2 μg/mL, diluted in Buffer A (20 mM Tris pH 7.5, 0.15 M NaCl, and 1 mM each of $MgCl_2$, $CaCl_2$, and $MnCl_2$). After overnight incubation at 4° C., the plate was blocked for 1 hour at 30° C., with 3.5% BSA in Buffer B (50 mM Tris pH 7.5, 0.1 M NaCl, and 1 mM each of $MgCl_2$, $CaCl_2$, and $MnCl_2$). After washing 3 times with Buffer B, diluted peptide or protein solutions were combined with 3.5 nM biotinylated fibrinogen in 0.1% BSA/Buffer B and added to the wells, incubating at 30° C. for 2 hr. After washing (3 times, Buffer B), 1:4000 streptavidin-horseradish peroxidase (HRP) was added (Pierce Chemical Co., Rockford, Ill.) for 1 hour at 30° C. After a final washing step (3 times, Buffer B), the plate was developed with Ultra TMB (3,3',5,5'-tetramentylbenzidine) (Pierce Chemical Co., Rockford, Ill.) for 5 minutes, stopping with an equal volume of 2 M sulfuric acid. Plate absorbances were read at 450 nm, and $IC_{50}$ values determined using a 4-parameter logistic fit.

The modified integrilin peptide (BHRF1) is then coupled with FVIII via the cysteine (Cys) residue located in the B-domain of FVIII.

Example 2

Coupling GPIIb/IIIa Binding Peptides to FVIII

The polypeptide sequence of the full-length FVIII is known in the art (see, e.g., SEQ ID NO: 1, SEQ ID NO: 2, and as disclosed in WO 2006/053299).

Concentration of FVIII and Uncapping of Free Sulfhydryl Groups

The Cys residue located in the B-domain of recombinant FVIII can be capped by cysteine present in the media during protein expression, but it can be readily removed by treatment with reducing agents, such as TCEP, as follows. FVIII (20 mL) was thawed and concentrated in two Amicon®-15 cartridges (Millipore, Billerica, Mass.), spun at 2000×g (about 3153 rpm) for 25 minutes in the cold. The concentration of the 2.8 mL retentate is about 0.8-0.9 mg/mL by A280 using a NanoDrop® spectrophotometer (ThermoFisher Scientific, Waltham, Mass.). The buffer was then exchanged using a 10 mL Zeba desalting cartridge, pre-equilibrated with 50 mM Tris, 150 mM NaCl, 2.5 mM $CaCl_2$ and 100 ppm Tween®-80 (polyoxyethylenesorbitan monooleate). A protein solution of 2.8 mL with a concentration of 0.88 mg/mL was obtained. TCEP was then added to a final concentration of 0.68 mM and the mixture was gently turned end-over-end at 4° C. for about 3 hours. TCEP was removed by two successive Zeba cartridge spins, and the FVIII was allowed to re-oxidize for at least 30 minutes before addition of the peptide. After the removal of TCEP, the FVIII concentration was measured at 0.768 mg/mL ("KG-R").

Coupling of the RGD Targeting Peptide

To couple the modified integrilin peptide BHRF-1 to FVIII, 0.294 mg of the peptide (M.W. 1225) was added to 48 μL dry dimethyl sulfoxide (DMSO) to make a 5 mM stock solution. This stock solution (34.4 μL) was then added to 2.8 mL KG-R. The reaction was quenched by addition of an equi-molar amount of cysteine after 80 minutes. The reaction mixture was then extensively dialyzed against starting Tris buffer (2 liters). The final concentration of BHRF-1-FVIII was 0.74 mg/mL and the yield was 2 mg. A similar procedure was also used to prepare BHRF-3-FVIII.

As shown in FIG. 3, the modified integrilin peptides, BHRF-1 and BHRF-3, retain affinity for GPIIb/IIIa as they potently blocked fibrinogen (Fbn) binding to immobilized GPIIa/IIIb. FVIII coupled to BHRF-1 (FVIII-BHRF-1) showed high potency for inhibition of fibrinogen binding to immobilized GPIIb/IIIa ($IC_{50}$=0.043+/−0.05 nM (N=3)). This was even more potent than the parent BHRF-1 peptide. Results are shown in Table 1.

TABLE 1

| Conjugate Moiety | nM | (N) |
|---|---|---|
| Integrelin | 1.3 +/− 1.0 | 4 |
| BHRF-1 (+linker) | 1.2 +/− 0.6 | 2 |
| BHRF-3 (+linker + FITC) | 1.5 +/− 1.3 | 3 |

Coupling of the RGD Targeting Peptide to B-Domain Deleted FVIII

If a B-domain deleted FVIII ("BDD") is used for coupling, a variety of Cys muteins of B-domain deleted FVIII as disclosed in WO 2006/053299 can be used to couple BDD to a targeting domain such as the modified RGD peptides as disclosed herein.

Example 3

BHRF-1-FVIII Binds to Immobilized GPIIb/IIIa

Figure 6:
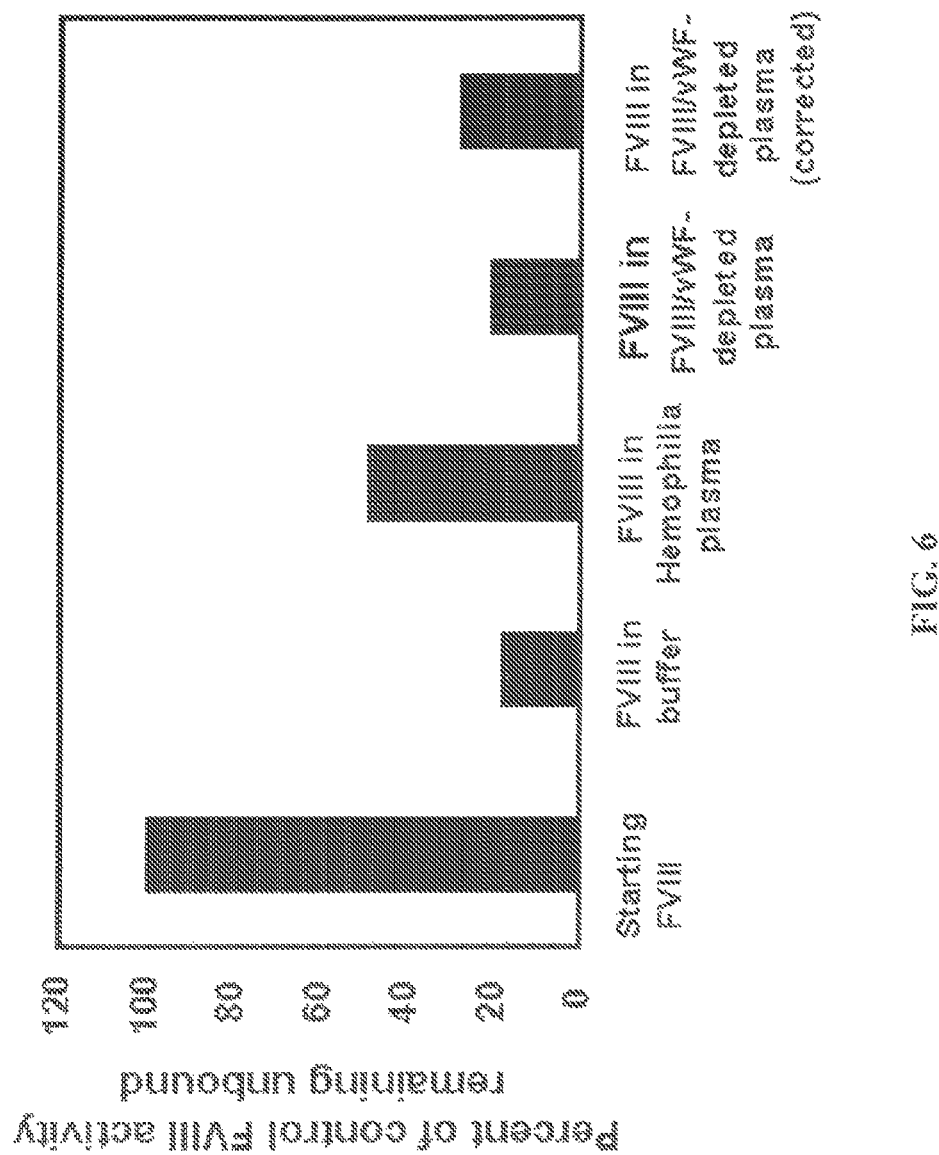
FIG. 6: In vitro binding of BHRF-1-FVIII to human platelets.

To test the binding activity of BHRF-1-FVIII to GPIIb/IIIa, biotinylated GPIIb/IIIa was immobilized on streptavidin plates and treated with either BHRF-1-FVIII or unmodified FVIII, both in binding buffer (50 mM Tris, pH 7.5, 100 mM $NaCl_2$, 1 mM $CaCl_2$, 1 mM $MgCl_2$, 1 mM $MnCl_2$ and 1 mg/mL BSA). The unbound protein was removed by washing three times with binding buffer. Assay buffer (25 μL) was added to the plate, and FVIII activity was determined using a chromogenic assay kit (Coatest® SP4, Chromogenix, Lexington, Mass.). As shown in FIG. 4, there was binding of BHRF-1-FVIII, while only little binding of unmodified FVIII was detected. The increased binding of BHRF-1-FVIII was completely eliminated by addition of a cyclic RGD peptide (GpenGRGDSPCA; SEQ ID NO: 5) that competes for BHRF-1 binding to GPIIb/IIIa. Furthermore, only low background levels of either protein bound when no GPIIb/IIIa was immobilized on the plate. These data show that BHRF-1-FVIII can be targeted to GPIIB/IIIa through the peptide targeting domain.

Because unconjugated FVIII was not removed from the preparations of BHRF1-FVIII, experiments were performed to determine the amount of unconjugated FVIII present. BHRF1-FVIII activity was depleted using beads containing excess levels of immobilized GPIIb/IIIa. Roughly 80% of the activity of BHRF1-FVIII can be depleted, indicating about 20% of the FVIII activity in the preparation came from unconjugated FVIII.

Example 4

In Vitro Whole Blood Clotting Activity Assay with BHRF-1-FVIII and FVIII

To assess the effect of platelet binding of BHRF-1-FVIII on hemostatic activity, its activity was compared to that of unconjugated FVIII using a Rotational Thromboelastometry (ROTEM®, Pentapharm GmbH) system as described in Landskroner, et al, (Haemophilia 11:346-352, 2005). Unlike measures of clotting activity such as the Coatest® chromogenic assay or the activated partial thromboplastin time (aPTT) assay, the ROTEM® assay depends on the function of the platelets and therefore, can show effects of BHRF-1-FVIII binding to platelets. To perform the assay, citrated hemophilia A mouse whole blood was mixed with an equal dose of BHRF-1-FVIII (1 mIU) or unconjugated FVIII (based on the Coatest® chromogenic assay) at room temperature. Samples were recalcified by dispensing 300 μL treated blood with an automated pipette into ROTEM® cups with 20 μL $CaCl_2$ (200 mmol) without exogenous activator (NATEM). Measurement was started immediately after the last pipetting and blood clot formation was continuously monitored for 2 hours (7200 seconds) at 37° C.

ROTEM® analysis parameters for hemostasis include Clotting Time (CT), the time required to obtain clot firmness of 2 mm following the initiation of measurement, Clot Formation Time (CFT), the time from clot firmness of 2 mm till clot strength of 20 mm, and α-angle, the velocity of clot formation.

As shown in FIG. 5, BHRF-1-FVIII required less time to form a clot in the ROTEM® assay than an equal dose (based on a chromogenic assay) of unconjugated FVIII, indicating a higher efficiency of clotting. The difference in CT was about 400 seconds, which corresponds to roughly 2-3 fold more FVIII activity, based on FVIII standard curves.

Hemostatic activity and pharmacokinetic parameter of targeted coagulation factors can be assessed in vivo using the hemophilia A mouse model. Targeted coagulation factors can be administered by tail vein intravenous injection. At multiple time points after the treatment, blood will be collected in % sodium citrate and hemostatic activity will be measured using ROTEM® over 48 hours post infusion period, which is equivalent to >6 half-life of FVIII ($t_{1/2}$) in mice.

Example 5

In Vitro Binding Assay to Human and Mouse Platelets Binding of FVIII-BHRF-1 to Human Platelets Human platelets were obtained from Allcells (Emeryville, Calif.) at $5\times10^9$ platelets/tube in 14 mL plasma. The platelets and all washes, buffers, reagents, and centrifuges were warmed to room temperature and maintained at room temperature during the course of the experiment. The wash buffer (WB) for the platelets is Tyrode's buffer supplemented with 20 mM HEPES, 0.5% BSA, and 50 ng/mL PGE1 and 2.5 U/mL apyrase, pH 7.4.

The cells were centrifuged at 700×g for 15 minutes at 25° C., and then the supernatant was carefully removed and 14 mL WB was added. The cells were gently re-suspended in the WB and centrifuged as described.

Following the second centrifugation, the supernatant was removed and the platelets were re-suspended in 15 mL WB. At this point, the cells were split into three equal aliquots of 5 mL each. The three aliquots were centrifuged as described earlier, and then the three platelet pellets were re-suspended in either:

A. 5 mL binding buffer+5 mg/mL BSA (BBB, 50 mM Tris, 100 mM NaCl, 1 mM each $CaCl_2$, $MgCl_2$, and $MnCl_2$)

B. 5 mL HemA plasma which lacks FVIII, but vWF is present

C. 5 mL immuno-depleted plasma lacking both FVIII and vWF.

For buffer (A) or plasma (B or C), the following conditions were used:

1. buffer/plasma alone+2.5 nM BHRF-1-FVIII (containing about 20% uncongugated FVIII (see Example 3))
2. buffer/plasma+platelet+2.5 nM BHRF-1-FVIII (containing about 20% uncongugated FVIII)
3. buffer/plasma alone+2.5 nM recombinant FVIII
4. buffer/plasma+platelet+2.5 nM recombinant FVIII For each condition 1-4, 100 μL A, B, or C was pipetted into a microfuge tube at room temperature, then the BHRF-1-FVIII or unconjugated FVIII was added to the tube. The tubes were incubated at 37° C. for 1.5 hours (without shaking). Following the incubation period, the tubes were centrifuged at maximum speed (16,000 rpm) for 5 minutes to pellet the platelets. The supernatant was collected to assay for FVIII activity. The amount of activity in the supernatant reflects the amount of unbound FVIII or BHRF-1-FVIII. The data demonstrate binding of the BHRF1-FVIII to human platelets in all conditions (shown in FIG. 6). Since the BHRF-1-FVIII contains roughly 20% unconjugated FVIII for conditions A and C, the data indicate that a high percentage of conjugate was bound. There was no binding of FVIII observed for conditions A and B, while 35% of the FVIII activity was bound in condition C. The figure also shows the level of FVIII activity remaining for condition C corrected for the 35% non-specific binding of FVIII were observed for this condition (i.e., the starting FVIII activity was reduced by 35% to calculate the percentage bound).

Binding of FVIII-BHRF-1 to Mouse Platelets

Figure 7:
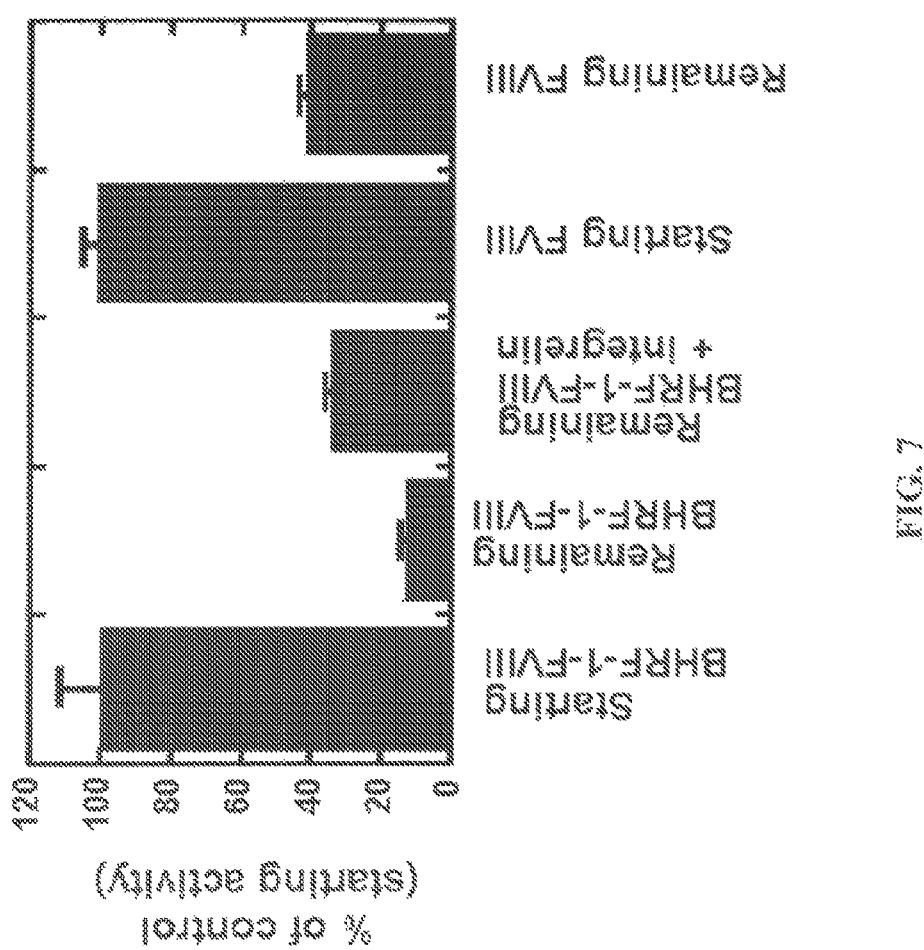
FIG. 7: In vitro binding of BHRF-1-FVIII to mouse platelets.

BHRF-1-FVIII also bound to mouse platelets as shown in FIG. 7. A similar binding assay was performed as described for human platelets except that citrated mouse blood was centrifuged 200×g for 15 minutes to harvest platelet rich plasma (PRP). The PRP was diluted with citrate wash buffer (11 mM glucose, 128 mM NaCl, 4.3 mM $NaH_2PO_4$, 7.5 mM $Na_2HPO_4$, 4.8 mM Na-citrate, 2.4 mM citric acid, 0.35% BSA, pH 6.5)+50 ng/mL PGE1, and washed twice in citrate wash buffer+50 ng/mL PGE1 (by centrifuging at 1200×g for 10 minutes). The platelets were finally re-suspended in binding buffer (50 mM Tris, 100 mM NaCl, 1 mM each $CaCl_2$, $MgCl_2$, and $MnCl_2$)+5 mg/mL BSA. Un-conjugated FVIII and BHRF-1-FVIII were added to the platelets and after 2 hours at 37° C., the platelets were removed by centrifugation, and the unbound FVIII activity in the supernatant determined.

As shown in the FIG. 7, 59% of the activity of unconjugated FVIII bound to the platelets. To calculate the percentage of the added BHRF-1-FVIII activity binding to platelets through the BHRF-1 peptide, the amount of starting FVIII activity was corrected by 59% to reflect the level of non-specific binding of FVIII (not occurring through the peptide). The corrected value for BHRF-1-FVIII was 31% unbound (69% bound). When 100 uM integrilin was added to complete for peptide binding, unbound activity rose to 82% unbound (18% bound) (also corrected for nonspecific FVIII binding). These data demonstrate that BHRF-1-FVIII can bind to mouse platelets through the BHRF-1 targeting domain.

Example 6

Pharmacokinetic Study

The level of FVIII in blood at various times after injection into hemophilia A mice is determined using a whole blood coagulation assay such as ROTEM® described above, which reflects FVIII activity in both plasma and bound to cells (e.g., platelets).

Example 7

Chromogenic Assay for the Assessment of FVIII Activity

FVIII activity of purified proteins and conjugates was assessed using the Coatest® SP assay kit (Chromogenix, Lexington, Mass.). The assay was performed following the manufacturer's instructions in a 96-well plate format. Briefly, diluted samples containing FVIII or conjugate were combined in order with a mixture of activated FIX/FX/phospholipid, followed by 25 mM $CaCl_2$ and chromogenic substrate S-2765/I-2581. Between each reagent addition, the samples were incubated at 37° C. for 5 minutes. After the final addition of chromogenic substrate, the reaction was stopped after 5 minutes with 20% acetic acid and the plate absorbances were read at 405 nm, normalized against a 490 nm background. Sample absorbances were calibrated against a WHO/NIBSC plasma-derived FVIII standard curve with an operating range of 0.3-40 mIU/mL.

Example 8

In Vivo Efficacy Assay in Hemophilic Mice

To show the efficacy of targeted FVIII molecules in promoting blood clotting and to assess the duration of these effects, the tail clip injury or tail vein transection models, which use hemophilic (HemA) mice, can be used as described below.

Tail Clip Injury Model

Test samples are administrated to the mice via a tail vein injection. Following administration, the mice are anesthetized intraperitoneal (IP) with ketamine/xylazine (100 mg/kg, 10 mg/kg). When the animals are fully anesthetized, the tails are placed individually in 13 mL 37° C. pre-warmed saline for approximately 10 minutes. A tail cut is made with a sharp scalpel and the tail is placed immediately in a new tube with 9 mL 37° C. warm saline. Blood is collected continuously for 30 minutes. Blood loss volume is determined either by weight gain of the blood collection tube or determined by the optical density of the blood/saline mixture in the blood collection tube.

Tail Vein Transection

HemA male mice are randomized into different treatment groups by their body weight. Mice are dosed by tail vein injection 24 hours prior to the tail vein transection. Before the tail vein transection, mice are anesthetized (IP) with a cocktail containing 50 μg/kg of ketamine and 1 mg/kg of medetomidine. The tail is marked at a diameter of 2.7 mm using a french catheter. The anesthetic effect of medetomidine is reversed with 1 mg/kg of atipamezole by IP injection. The tail vein is transected with a scalpel blade. The tail is then submerged into 37° C. saline tube, and the tube is rotated to rinse away the blood from the cut. When the saline becomes too opaque to visualize, it is replaced with a new tube until the tail stops bleeding. The time it takes to stop bleeding is recorded as the acute clotting time. The mouse is then returned to its individual clean cage with white paper bedding placed on top of a 4×8 inch heating pad. The time to re-bleed and moribund is monitored hourly for the next 9-11 hours for excessive blood loss.

Example 9

Recombinant Expression of Targeted FVIII

In one embodiment, HKB11 cells are grown in suspension culture on an orbital shaker (100-125 rpm) in a 5% $CO_2$ incubator at 37° C. in a protein-free media and maintained at a density between 0.25 and 1.5×10$^6$ cells/mL. HKB11 cells for transfection are collected by centrifugation then resuspended in an expression medium such as FreeStyle™ 293 Expression Medium (Invitrogen, Carlsbad, Calif.) at 1.1×10$^6$ cells/mL. The cells are seeded in 6-well plates (4.6 mL/well) and incubated on an orbital rotator (125 rpm) in a 37° C. $CO_2$ incubator. For each well, 5 μg plasmid DNA is mixed with 0.2 mL Opti-MEM® I medium (Invitrogen, Carlsbad, Calif.).

For each well, 7 μL 293Fectin™ reagent (Invitrogen, Carlsbad, Calif.) is mixed gently with 0.2 mL Opti-MEM® I medium and incubated at room temperature for 5 minutes. The diluted 293Fectin™ is added to the diluted DNA solution, mixed gently, incubated at room temperature for 20-30 minutes, and then added to each well that has been seeded with 5×10$^6$ (4.6 mL) HKB11 cells. The cells are then incubated on an orbital rotator (125 rpm) in a $CO_2$ incubator at 37° C. for 3 days after which the cells are pelleted by centrifugation at 1000 rpm for 5 minutes and the supernatant is collected.

Stable transfection of HKB11 cells is obtained using the following procedure. HKB11 cells are transfected with plasmid DNA using 293Fectin™ reagent as described in transient transfection. The transfected cells are split into 100-mm culture dishes at various dilutions (1:100, 1:1000, 1;10,000) and maintained in DMEM-F12 medium supplemented with 5% FBS and 200 ug/mL hygromicin (Invitrogen, Carlsbad, Calif.) for about 2 weeks. Individual single colonies are picked and transferred into 6-well plates using sterile cloning disks (Scienceware®, Sigma-Aldrich, St. Louis, Mo.). The clones are established and banked. These clones are screened for high expression of the fusion protein by FVIII activity assays (e.g., Coatest® and aPTT assays) as well as by FVIII ELISA.

Factor VIII activity levels in culture supernatants and purification fractions may be determined using a commercial chromogenic assay kit (Coatest® SP4 FVIII, Chromogenix, Lexington, Mass.) in a 96-well format as described above. Factor VIII coagulation activity may also be determined using an aPTT assay in FVIII-deficient human plasma by an Electra® 1800 C automatic coagulation analyzer (Beckman Coulter, Fullerton, Calif.). Briefly, three dilutions of supernatant samples in coagulation diluent are created by the instrument and 100 μL is then mixed with 100 μL FVIII-deficient plasma and 100 μL automated aPTT reagent (rabbit brain phospholipid and micronized silica, Biomerieux, Durham, N.C.). After the addition of 100 μL 25 mM $CaCl_2$ solution, the time to clot formation is recorded. A standard curve is generated for each run using serial dilutions of the same purified FVIII used as the standard in the ELISA assay.

While the present invention has been described with reference to the specific embodiments and examples, it should be understood that various modifications and changes may be made and equivalents may be substituted without departing from the true spirit and scope of the invention. The specification and examples are, accordingly, to be regarded in an illustrative rather then a restrictive sense. Furthermore, all articles, patent applications and patents referred to herein are incorporated herein by reference in their entireties.

---

The invention claimed is:

1. A Factor VIII molecule comprising an amino acid sequence that is at least 95% identical to the mature portion of an amino acid sequence selected from the group consisting of SEQ. ID NO: 1, and SEQ ID NO: 2, which molecule is covalently attached to a platelet specific molecule, wherein said platelet specific molecule is a single chain GPIIb/IIIa antibody fragment.

2. A Factor VIII molecule as recited in claim 1, wherein the platelet specific molecule is fused to the Factor VIII molecule.

3. A Factor VIII molecule as recited in claim 1, wherein the platelet specific molecule is fused to the B-domain or a portion of the B-domain of Factor VIII.

4. A Factor VIII molecule as recited in claim 1, wherein the Factor VIII molecule further comprises a C-terminus and the platelet specific molecule is fused to the C-terminus of the Factor VIII molecule.

5. A Factor VIII molecule as recited in claim 1, wherein said molecule has reduced von Willebrand factor binding capacity.

6. A Factor VIII molecule as recited in claim 1, wherein said molecule has increased binding affinity to a platelet in the absence of von Willebrand factor.

7. A Factor VIII molecule as recited in claim 1, wherein said single chain GPIIb/IIIa antibody fragment is covalently attached to Factor VIII via a cysteine residue.

8. A Factor VIII molecule as recited in claim 7, wherein said cysteine residue is located in a B-domain of a B domain truncated Factor VIII molecule.

9. A Factor VIII molecule according to claim 1, wherein the a3 domain of the Factor VIII molecule is replaced with the single chain GPIIb/IIIa antibody fragment.

10. A nucleic acid encoding a Factor VIII molecule according to claim 1.

11. A host cell comprising a nucleic acid according to claim 10.

12. A method of producing a Factor VIII molecule said method comprising expressing the nucleic acid according to claim 10 in a host cell.

13. A method of producing a Factor VIII molecule according to claim 1, wherein said method comprises conjugation of the FVIII molecule with the single chain GPIIb/IIIa antibody fragment.

14. A pharmaceutical composition comprising a Factor VIII molecule according to claim 1.

15. A Factor VIII molecule according to claim 1 for use in a method for the treatment of hemophilia A or von Willebrand Disease.

* * * * *

SEQUENCE LISTING

```
<160> NUMBER OF SEQ ID NOS: 7

<210> SEQ ID NO 1
<211> LENGTH: 2351
<212> TYPE: PRT
<213> ORGANISM: Homo sapiens

<400> SEQUENCE: 1

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Val His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
                180                 185                 190

Gly Ala Leu Leu Val Cys Arg Glu Gly Ser Leu Ala Lys Glu Lys Thr
```

```
            195                 200                 205
Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620
```

-continued

```
Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
            690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
            755                 760                 765

Ser Thr Arg Gln Lys Gln Phe Asn Ala Thr Thr Ile Pro Glu Asn Asp
770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
            835                 840                 845

Ser Leu Ser Glu Met Thr His Phe Arg Pro Gln Leu His His Ser Gly
850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
            915                 920                 925

Pro Val His Tyr Asp Ser Gln Leu Asp Thr Thr Leu Phe Gly Lys Lys
            930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
            995                 1000                1005

Leu Phe Lys Val Ser Ile Ser Leu Leu Lys Thr Asn Lys Thr Ser
        1010            1015            1020

Asn Asn Ser Ala Thr Asn Arg Lys Thr His Ile Asp Gly Pro Ser
        1025            1030            1035
```

-continued

| | | | | | | | | | | | |
|---|---|---|---|---|---|---|---|---|---|---|---|
| Leu | Leu | Ile | Glu | Asn | Ser | Pro | Ser | Val | Trp | Gln | Asn | Ile | Leu | Glu |
| 1040 | | | | | 1045 | | | | | 1050 | | | | |
| Ser | Asp | Thr | Glu | Phe | Lys | Lys | Val | Thr | Pro | Leu | Ile | His | Asp | Arg |
| 1055 | | | | | 1060 | | | | | 1065 | | | | |
| Met | Leu | Met | Asp | Lys | Asn | Ala | Thr | Ala | Leu | Arg | Leu | Asn | His | Met |
| 1070 | | | | | 1075 | | | | | 1080 | | | | |
| Ser | Asn | Lys | Thr | Thr | Ser | Ser | Lys | Asn | Met | Glu | Met | Val | Gln | Gln |
| 1085 | | | | | 1090 | | | | | 1095 | | | | |
| Lys | Lys | Glu | Gly | Pro | Ile | Pro | Pro | Asp | Ala | Gln | Asn | Pro | Asp | Met |
| 1100 | | | | | 1105 | | | | | 1110 | | | | |
| Ser | Phe | Phe | Lys | Met | Leu | Phe | Leu | Pro | Glu | Ser | Ala | Arg | Trp | Ile |
| 1115 | | | | | 1120 | | | | | 1125 | | | | |
| Gln | Arg | Thr | His | Gly | Lys | Asn | Ser | Leu | Asn | Ser | Gly | Gln | Gly | Pro |
| 1130 | | | | | 1135 | | | | | 1140 | | | | |
| Ser | Pro | Lys | Gln | Leu | Val | Ser | Leu | Gly | Pro | Glu | Lys | Ser | Val | Glu |
| 1145 | | | | | 1150 | | | | | 1155 | | | | |
| Gly | Gln | Asn | Phe | Leu | Ser | Glu | Lys | Asn | Lys | Val | Val | Val | Gly | Lys |
| 1160 | | | | | 1165 | | | | | 1170 | | | | |
| Gly | Glu | Phe | Thr | Lys | Asp | Val | Gly | Leu | Lys | Glu | Met | Val | Phe | Pro |
| 1175 | | | | | 1180 | | | | | 1185 | | | | |
| Ser | Ser | Arg | Asn | Leu | Phe | Leu | Thr | Asn | Leu | Asp | Asn | Leu | His | Glu |
| 1190 | | | | | 1195 | | | | | 1200 | | | | |
| Asn | Asn | Thr | His | Asn | Gln | Glu | Lys | Lys | Ile | Gln | Glu | Glu | Ile | Glu |
| 1205 | | | | | 1210 | | | | | 1215 | | | | |
| Lys | Lys | Glu | Thr | Leu | Ile | Gln | Glu | Asn | Val | Val | Leu | Pro | Gln | Ile |
| 1220 | | | | | 1225 | | | | | 1230 | | | | |
| His | Thr | Val | Thr | Gly | Thr | Lys | Asn | Phe | Met | Lys | Asn | Leu | Phe | Leu |
| 1235 | | | | | 1240 | | | | | 1245 | | | | |
| Leu | Ser | Thr | Arg | Gln | Asn | Val | Glu | Gly | Ser | Tyr | Glu | Gly | Ala | Tyr |
| 1250 | | | | | 1255 | | | | | 1260 | | | | |
| Ala | Pro | Val | Leu | Gln | Asp | Phe | Arg | Ser | Leu | Asn | Asp | Ser | Thr | Asn |
| 1265 | | | | | 1270 | | | | | 1275 | | | | |
| Arg | Thr | Lys | Lys | His | Thr | Ala | His | Phe | Ser | Lys | Lys | Gly | Glu | Glu |
| 1280 | | | | | 1285 | | | | | 1290 | | | | |
| Glu | Asn | Leu | Glu | Gly | Leu | Gly | Asn | Gln | Thr | Lys | Gln | Ile | Val | Glu |
| 1295 | | | | | 1300 | | | | | 1305 | | | | |
| Lys | Tyr | Ala | Cys | Thr | Thr | Arg | Ile | Ser | Pro | Asn | Thr | Ser | Gln | Gln |
| 1310 | | | | | 1315 | | | | | 1320 | | | | |
| Asn | Phe | Val | Thr | Gln | Arg | Ser | Lys | Arg | Ala | Leu | Lys | Gln | Phe | Arg |
| 1325 | | | | | 1330 | | | | | 1335 | | | | |
| Leu | Pro | Leu | Glu | Glu | Thr | Glu | Leu | Glu | Lys | Arg | Ile | Ile | Val | Asp |
| 1340 | | | | | 1345 | | | | | 1350 | | | | |
| Asp | Thr | Ser | Thr | Gln | Trp | Ser | Lys | Asn | Met | Lys | His | Leu | Thr | Pro |
| 1355 | | | | | 1360 | | | | | 1365 | | | | |
| Ser | Thr | Leu | Thr | Gln | Ile | Asp | Tyr | Asn | Glu | Lys | Glu | Lys | Gly | Ala |
| 1370 | | | | | 1375 | | | | | 1380 | | | | |
| Ile | Thr | Gln | Ser | Pro | Leu | Ser | Asp | Cys | Leu | Thr | Arg | Ser | His | Ser |
| 1385 | | | | | 1390 | | | | | 1395 | | | | |
| Ile | Pro | Gln | Ala | Asn | Arg | Ser | Pro | Leu | Pro | Ile | Ala | Lys | Val | Ser |
| 1400 | | | | | 1405 | | | | | 1410 | | | | |
| Ser | Phe | Pro | Ser | Ile | Arg | Pro | Ile | Tyr | Leu | Thr | Arg | Val | Leu | Phe |
| 1415 | | | | | 1420 | | | | | 1425 | | | | |
| Gln | Asp | Asn | Ser | Ser | His | Leu | Pro | Ala | Ala | Ser | Tyr | Arg | Lys | Lys |

-continued

```
                1430                1435                1440

Asp Ser Gly Val Gln Glu Ser His Phe Leu Gln Gly Ala Lys
    1445                1450                1455

Lys Asn Asn Leu Ser Leu Ala Ile Leu Thr Leu Glu Met Thr Gly
    1460                1465                1470

Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Gly Thr
    1535                1540                1545

Glu Gly Ala Ile Lys Trp Asn Glu Ala Asn Arg Pro Gly Lys Val
    1550                1555                1560

Pro Phe Leu Arg Val Ala Thr Glu Ser Ser Ala Lys Thr Pro Ser
    1565                1570                1575

Lys Leu Leu Asp Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ala Ile Asn Glu Gly Gln Asn Lys
    1625                1630                1635

Pro Glu Ile Glu Val Thr Trp Ala Lys Gln Gly Arg Thr Glu Arg
    1640                1645                1650

Leu Cys Ser Gln Asn Pro Pro Val Leu Lys Arg His Gln Arg Glu
    1655                1660                1665

Ile Thr Arg Thr Thr Leu Gln Ser Asp Gln Glu Glu Ile Asp Tyr
    1670                1675                1680

Asp Asp Thr Ile Ser Val Glu Met Lys Lys Glu Asp Phe Asp Ile
    1685                1690                1695

Tyr Asp Glu Asp Glu Asn Gln Ser Pro Arg Ser Phe Gln Lys Lys
    1700                1705                1710

Thr Arg His Tyr Phe Ile Ala Ala Val Glu Arg Leu Trp Asp Tyr
    1715                1720                1725

Gly Met Ser Ser Ser Pro His Val Leu Arg Asn Arg Ala Gln Ser
    1730                1735                1740

Gly Ser Val Pro Gln Phe Lys Lys Val Val Phe Gln Glu Phe Thr
    1745                1750                1755

Asp Gly Ser Phe Thr Gln Pro Leu Tyr Arg Gly Glu Leu Asn Glu
    1760                1765                1770

His Leu Gly Leu Leu Gly Pro Tyr Ile Arg Ala Glu Val Glu Asp
    1775                1780                1785

Asn Ile Met Val Thr Phe Arg Asn Gln Ala Ser Arg Pro Tyr Ser
    1790                1795                1800

Phe Tyr Ser Ser Leu Ile Ser Tyr Glu Glu Asp Gln Arg Gln Gly
    1805                1810                1815

Ala Glu Pro Arg Lys Asn Phe Val Lys Pro Asn Glu Thr Lys Thr
    1820                1825                1830
```

```
Tyr Phe Trp Lys Val Gln His His Met Ala Pro Thr Lys Asp Glu
    1835            1840                1845

Phe Asp Cys Lys Ala Trp Ala Tyr Phe Ser Asp Val Asp Leu Glu
    1850            1855                1860

Lys Asp Val His Ser Gly Leu Ile Gly Pro Leu Leu Val Cys His
    1865            1870                1875

Thr Asn Thr Leu Asn Pro Ala His Gly Arg Gln Val Thr Val Gln
    1880            1885                1890

Glu Phe Ala Leu Phe Phe Thr Ile Phe Asp Glu Thr Lys Ser Trp
    1895            1900                1905

Tyr Phe Thr Glu Asn Met Glu Arg Asn Cys Arg Ala Pro Cys Asn
    1910            1915                1920

Ile Gln Met Glu Asp Pro Thr Phe Lys Glu Asn Tyr Arg Phe His
    1925            1930                1935

Ala Ile Asn Gly Tyr Ile Met Asp Thr Leu Pro Gly Leu Val Met
    1940            1945                1950

Ala Gln Asp Gln Arg Ile Arg Trp Tyr Leu Leu Ser Met Gly Ser
    1955            1960                1965

Asn Glu Asn Ile His Ser Ile His Phe Ser Gly His Val Phe Thr
    1970            1975                1980

Val Arg Lys Lys Glu Glu Tyr Lys Met Ala Leu Tyr Asn Leu Tyr
    1985            1990                1995

Pro Gly Val Phe Glu Thr Val Glu Met Leu Pro Ser Lys Ala Gly
    2000            2005                2010

Ile Trp Arg Val Glu Cys Leu Ile Gly Glu His Leu His Ala Gly
    2015            2020                2025

Met Ser Thr Leu Phe Leu Val Tyr Ser Asn Lys Cys Gln Thr Pro
    2030            2035                2040

Leu Gly Met Ala Ser Gly His Ile Arg Asp Phe Gln Ile Thr Ala
    2045            2050                2055

Ser Gly Gln Tyr Gly Gln Trp Ala Pro Lys Leu Ala Arg Leu His
    2060            2065                2070

Tyr Ser Gly Ser Ile Asn Ala Trp Ser Thr Lys Glu Pro Phe Ser
    2075            2080                2085

Trp Ile Lys Val Asp Leu Leu Ala Pro Met Ile Ile His Gly Ile
    2090            2095                2100

Lys Thr Gln Gly Ala Arg Gln Lys Phe Ser Ser Leu Tyr Ile Ser
    2105            2110                2115

Gln Phe Ile Ile Met Tyr Ser Leu Asp Gly Lys Lys Trp Gln Thr
    2120            2125                2130

Tyr Arg Gly Asn Ser Thr Gly Thr Leu Met Val Phe Phe Gly Asn
    2135            2140                2145

Val Asp Ser Ser Gly Ile Lys His Asn Ile Phe Asn Pro Pro Ile
    2150            2155                2160

Ile Ala Arg Tyr Ile Arg Leu His Pro Thr His Tyr Ser Ile Arg
    2165            2170                2175

Ser Thr Leu Arg Met Glu Leu Met Gly Cys Asp Leu Asn Ser Cys
    2180            2185                2190

Ser Met Pro Leu Gly Met Glu Ser Lys Ala Ile Ser Asp Ala Gln
    2195            2200                2205

Ile Thr Ala Ser Ser Tyr Phe Thr Asn Met Phe Ala Thr Trp Ser
    2210            2215                2220
```

-continued

Pro Ser Lys Ala Arg Leu His Leu Gln Gly Arg Ser Asn Ala Trp
2225                2230                2235

Arg Pro Gln Val Asn Asn Pro Lys Glu Trp Leu Gln Val Asp Phe
2240                2245                2250

Gln Lys Thr Met Lys Val Thr Gly Val Thr Thr Gln Gly Val Lys
2255                2260                2265

Ser Leu Leu Thr Ser Met Tyr Val Lys Glu Phe Leu Ile Ser Ser
2270                2275                2280

Ser Gln Asp Gly His Gln Trp Thr Leu Phe Phe Gln Asn Gly Lys
2285                2290                2295

Val Lys Val Phe Gln Gly Asn Gln Asp Ser Phe Thr Pro Val Val
2300                2305                2310

Asn Ser Leu Asp Pro Pro Leu Leu Thr Arg Tyr Leu Arg Ile His
2315                2320                2325

Pro Gln Ser Trp Val His Gln Ile Ala Leu Arg Met Glu Val Leu
2330                2335                2340

Gly Cys Glu Ala Gln Asp Leu Tyr
2345                2350

<210> SEQ ID NO 2
<211> LENGTH: 2332
<212> TYPE: PRT
<213> ORGANISM: Homo sapiens

<400> SEQUENCE: 2

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Val His Leu Phe Asn Ile Ala Lys Pro
        50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

-continued

Ser Leu Pro Gly Leu Ile Gly Cys His Arg Lys Ser Val Tyr Trp His
            245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
            290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
            325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
            355                 360                 365

Ile Gln Ile Arg Ser Val Ala Lys Lys His Pro Lys Thr Trp Val His
            370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
            405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
            450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
            485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
            565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
            645                 650                 655

```
Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Ser Lys Asn Asn Ala
                725                 730                 735

Ile Glu Pro Arg Ser Phe Ser Gln Asn Ser Arg His Pro Ser Thr Arg
        740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
        770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
                820                 825                 830

Glu Met Thr His Phe Arg Pro Gln Leu His His Ser Gly Asp Met Val
                835                 840                 845

Phe Thr Pro Glu Ser Gly Leu Gln Leu Arg Leu Asn Glu Lys Leu Gly
        850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
        900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
        930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
                980                 985                 990

Val Ser Ile Ser Leu Leu Lys Thr Asn Lys Thr Ser Asn Asn Ser Ala
        995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
```

-continued

```
                1070                1075                1080
Pro Ile Pro Pro Asp Ala Gln Asn Pro Asp Met Ser Phe Phe Lys
        1085                1090                1095
Met Leu Phe Leu Pro Glu Ser Ala Arg Trp Ile Gln Arg Thr His
    1100                1105                1110
Gly Lys Asn Ser Leu Asn Ser Gly Gln Gly Pro Ser Pro Lys Gln
    1115                1120                1125
Leu Val Ser Leu Gly Pro Glu Lys Ser Val Glu Gly Gln Asn Phe
    1130                1135                1140
Leu Ser Glu Lys Asn Lys Val Val Val Gly Lys Gly Glu Phe Thr
    1145                1150                1155
Lys Asp Val Gly Leu Lys Glu Met Val Phe Pro Ser Ser Arg Asn
    1160                1165                1170
Leu Phe Leu Thr Asn Leu Asp Asn Leu His Glu Asn Asn Thr His
    1175                1180                1185
Asn Gln Glu Lys Lys Ile Gln Glu Glu Ile Glu Lys Lys Glu Thr
    1190                1195                1200
Leu Ile Gln Glu Asn Val Val Leu Pro Gln Ile His Thr Val Thr
    1205                1210                1215
Gly Thr Lys Asn Phe Met Lys Asn Leu Phe Leu Leu Ser Thr Arg
    1220                1225                1230
Gln Asn Val Glu Gly Ser Tyr Glu Gly Ala Tyr Ala Pro Val Leu
    1235                1240                1245
Gln Asp Phe Arg Ser Leu Asn Asp Ser Thr Asn Arg Thr Lys Lys
    1250                1255                1260
His Thr Ala His Phe Ser Lys Lys Gly Glu Glu Glu Asn Leu Glu
    1265                1270                1275
Gly Leu Gly Asn Gln Thr Lys Gln Ile Val Glu Lys Tyr Ala Cys
    1280                1285                1290
Thr Thr Arg Ile Ser Pro Asn Thr Ser Gln Gln Asn Phe Val Thr
    1295                1300                1305
Gln Arg Ser Lys Arg Ala Leu Lys Gln Phe Arg Leu Pro Leu Glu
    1310                1315                1320
Glu Thr Glu Leu Glu Lys Arg Ile Ile Val Asp Asp Thr Ser Thr
    1325                1330                1335
Gln Trp Ser Lys Asn Met Lys His Leu Thr Pro Ser Thr Leu Thr
    1340                1345                1350
Gln Ile Asp Tyr Asn Glu Lys Glu Lys Gly Ala Ile Thr Gln Ser
    1355                1360                1365
Pro Leu Ser Asp Cys Leu Thr Arg Ser His Ser Ile Pro Gln Ala
    1370                1375                1380
Asn Arg Ser Pro Leu Pro Ile Ala Lys Val Ser Ser Phe Pro Ser
    1385                1390                1395
Ile Arg Pro Ile Tyr Leu Thr Arg Val Leu Phe Gln Asp Asn Ser
    1400                1405                1410
Ser His Leu Pro Ala Ala Ser Tyr Arg Lys Lys Asp Ser Gly Val
    1415                1420                1425
Gln Glu Ser Ser His Phe Leu Gln Gly Ala Lys Lys Asn Asn Leu
    1430                1435                1440
Ser Leu Ala Ile Leu Thr Leu Glu Met Thr Gly Asp Gln Arg Glu
    1445                1450                1455
Val Gly Ser Leu Gly Thr Ser Ala Thr Asn Ser Val Thr Tyr Lys
    1460                1465                1470
```

```
Lys Val Glu Asn Thr Val Leu Pro Lys Pro Asp Leu Pro Lys Thr
1475                1480                1485

Ser Gly Lys Val Glu Leu Leu Pro Lys Val His Ile Tyr Gln Lys
1490                1495                1500

Asp Leu Phe Pro Thr Glu Thr Ser Asn Gly Ser Pro Gly His Leu
1505                1510                1515

Asp Leu Val Glu Gly Ser Leu Leu Gln Gly Thr Glu Gly Ala Ile
1520                1525                1530

Lys Trp Asn Glu Ala Asn Arg Pro Gly Lys Val Pro Phe Leu Arg
1535                1540                1545

Val Ala Thr Glu Ser Ser Ala Lys Thr Pro Ser Lys Leu Leu Asp
1550                1555                1560

Pro Leu Ala Trp Asp Asn His Tyr Gly Thr Gln Ile Pro Lys Glu
1565                1570                1575

Glu Trp Lys Ser Gln Glu Lys Ser Pro Glu Lys Thr Ala Phe Lys
1580                1585                1590

Lys Lys Asp Thr Ile Leu Ser Leu Asn Ala Cys Glu Ser Asn His
1595                1600                1605

Ala Ile Ala Ala Ile Asn Glu Gly Gln Asn Lys Pro Glu Ile Glu
1610                1615                1620

Val Thr Trp Ala Lys Gln Gly Arg Thr Glu Arg Leu Cys Ser Gln
1625                1630                1635

Asn Pro Pro Val Leu Lys Arg His Gln Arg Glu Ile Thr Arg Thr
1640                1645                1650

Thr Leu Gln Ser Asp Gln Glu Glu Ile Asp Tyr Asp Asp Thr Ile
1655                1660                1665

Ser Val Glu Met Lys Lys Glu Asp Phe Asp Ile Tyr Asp Glu Asp
1670                1675                1680

Glu Asn Gln Ser Pro Arg Ser Phe Gln Lys Lys Thr Arg His Tyr
1685                1690                1695

Phe Ile Ala Ala Val Glu Arg Leu Trp Asp Tyr Gly Met Ser Ser
1700                1705                1710

Ser Pro His Val Leu Arg Asn Arg Ala Gln Ser Gly Ser Val Pro
1715                1720                1725

Gln Phe Lys Lys Val Val Phe Gln Glu Phe Thr Asp Gly Ser Phe
1730                1735                1740

Thr Gln Pro Leu Tyr Arg Gly Glu Leu Asn Glu His Leu Gly Leu
1745                1750                1755

Leu Gly Pro Tyr Ile Arg Ala Glu Val Glu Asp Asn Ile Met Val
1760                1765                1770

Thr Phe Arg Asn Gln Ala Ser Arg Pro Tyr Ser Phe Tyr Ser Ser
1775                1780                1785

Leu Ile Ser Tyr Glu Glu Asp Gln Arg Gln Gly Ala Glu Pro Arg
1790                1795                1800

Lys Asn Phe Val Lys Pro Asn Glu Thr Lys Thr Tyr Phe Trp Lys
1805                1810                1815

Val Gln His His Met Ala Pro Thr Lys Asp Glu Phe Asp Cys Lys
1820                1825                1830

Ala Trp Ala Tyr Phe Ser Asp Val Asp Leu Glu Lys Asp Val His
1835                1840                1845

Ser Gly Leu Ile Gly Pro Leu Leu Val Cys His Thr Asn Thr Leu
1850                1855                1860
```

```
Asn Pro Ala His Gly Arg Gln Val Thr Val Gln Glu Phe Ala Leu
    1865                1870                1875

Phe Phe Thr Ile Phe Asp Glu Thr Lys Ser Trp Tyr Phe Thr Glu
    1880                1885                1890

Asn Met Glu Arg Asn Cys Arg Ala Pro Cys Asn Ile Gln Met Glu
    1895                1900                1905

Asp Pro Thr Phe Lys Glu Asn Tyr Arg Phe His Ala Ile Asn Gly
    1910                1915                1920

Tyr Ile Met Asp Thr Leu Pro Gly Leu Val Met Ala Gln Asp Gln
    1925                1930                1935

Arg Ile Arg Trp Tyr Leu Leu Ser Met Gly Ser Asn Glu Asn Ile
    1940                1945                1950

His Ser Ile His Phe Ser Gly His Val Phe Thr Val Arg Lys Lys
    1955                1960                1965

Glu Glu Tyr Lys Met Ala Leu Tyr Asn Leu Tyr Pro Gly Val Phe
    1970                1975                1980

Glu Thr Val Glu Met Leu Pro Ser Lys Ala Gly Ile Trp Arg Val
    1985                1990                1995

Glu Cys Leu Ile Gly Glu His Leu His Ala Gly Met Ser Thr Leu
    2000                2005                2010

Phe Leu Val Tyr Ser Asn Lys Cys Gln Thr Pro Leu Gly Met Ala
    2015                2020                2025

Ser Gly His Ile Arg Asp Phe Gln Ile Thr Ala Ser Gly Gln Tyr
    2030                2035                2040

Gly Gln Trp Ala Pro Lys Leu Ala Arg Leu His Tyr Ser Gly Ser
    2045                2050                2055

Ile Asn Ala Trp Ser Thr Lys Glu Pro Phe Ser Trp Ile Lys Val
    2060                2065                2070

Asp Leu Leu Ala Pro Met Ile Ile His Gly Ile Lys Thr Gln Gly
    2075                2080                2085

Ala Arg Gln Lys Phe Ser Ser Leu Tyr Ile Ser Gln Phe Ile Ile
    2090                2095                2100

Met Tyr Ser Leu Asp Gly Lys Lys Trp Gln Thr Tyr Arg Gly Asn
    2105                2110                2115

Ser Thr Gly Thr Leu Met Val Phe Phe Gly Asn Val Asp Ser Ser
    2120                2125                2130

Gly Ile Lys His Asn Ile Phe Asn Pro Pro Ile Ile Ala Arg Tyr
    2135                2140                2145

Ile Arg Leu His Pro Thr His Tyr Ser Ile Arg Ser Thr Leu Arg
    2150                2155                2160

Met Glu Leu Met Gly Cys Asp Leu Asn Ser Cys Ser Met Pro Leu
    2165                2170                2175

Gly Met Glu Ser Lys Ala Ile Ser Asp Ala Gln Ile Thr Ala Ser
    2180                2185                2190

Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val
    2210                2215                2220

Asn Asn Pro Lys Glu Trp Leu Gln Val Asp Phe Gln Lys Thr Met
    2225                2230                2235

Lys Val Thr Gly Val Thr Thr Gln Gly Val Lys Ser Leu Leu Thr
    2240                2245                2250

Ser Met Tyr Val Lys Glu Phe Leu Ile Ser Ser Ser Gln Asp Gly
```

```
              2255                2260                2265

His Gln  Trp Thr Leu Phe  Phe Gln Asn Gly Lys  Val Lys Val Phe
    2270              2275                2280

Gln Gly  Asn Gln Asp Ser  Phe Thr Pro Val Val  Asn Ser Leu Asp
    2285              2290                2295

Pro Pro  Leu Leu Thr Arg  Tyr Leu Arg Ile His  Pro Gln Ser Trp
    2300              2305                2310

Val His  Gln Ile Ala Leu  Arg Met Glu Val Leu  Gly Cys Glu Ala
    2315              2320                2325

Gln Asp  Leu Tyr
    2330

<210> SEQ ID NO 3
<211> LENGTH: 1457
<212> TYPE: PRT
<213> ORGANISM: Artificial Sequence
<220> FEATURE:
<223> OTHER INFORMATION: Derived from human Factor VIII sequence

<400> SEQUENCE: 3

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Asn Thr Ser Val Val
50                  55                  60

Tyr Lys Lys Thr Leu Phe Val Glu Phe Thr Val His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
```

-continued

```
            275                 280                 285
Phe Leu Glu Gly His Thr Phe Leu Val Arg Asn His Arg Gln Ala Ser
290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                        325                 330                 335

Asp Gly Met Glu Ala Tyr Val Lys Val Asp Ser Cys Pro Glu Pro
                340                 345                 350

Gln Leu Arg Met Lys Asn Asn Glu Glu Ala Glu Asp Tyr Asp Asp
            355                 360                 365

Leu Thr Asp Ser Glu Met Asp Val Val Arg Phe Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
690                 695                 700
```

-continued

```
Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
        995                 1000                1005

Asp Glu Thr Lys Ser Trp Tyr Phe Thr Glu Asn Met Glu Arg Asn
    1010                1015                1020

Cys Arg Ala Pro Cys Asn Ile Gln Met Glu Asp Pro Thr Phe Lys
    1025                1030                1035

Glu Asn Tyr Arg Phe His Ala Ile Asn Gly Tyr Ile Met Asp Thr
    1040                1045                1050

Leu Pro Gly Leu Val Met Ala Gln Asp Gln Arg Ile Arg Trp Tyr
    1055                1060                1065

Leu Leu Ser Met Gly Ser Asn Glu Asn Ile His Ser Ile His Phe
    1070                1075                1080

Ser Gly His Val Phe Thr Val Arg Lys Lys Glu Glu Tyr Lys Met
    1085                1090                1095

Ala Leu Tyr Asn Leu Tyr Pro Gly Val Phe Glu Thr Val Glu Met
    1100                1105                1110
```

```
Leu Pro Ser Lys Ala Gly Ile Trp Arg Val Glu Cys Leu Ile Gly
    1115                1120                1125

Glu His Leu His Ala Gly Met Ser Thr Leu Phe Leu Val Tyr Ser
    1130                1135                1140

Asn Lys Cys Gln Thr Pro Leu Gly Met Ala Ser Gly His Ile Arg
    1145                1150                1155

Asp Phe Gln Ile Thr Ala Ser Gly Gln Tyr Gly Gln Trp Ala Pro
    1160                1165                1170

Lys Leu Ala Arg Leu His Tyr Ser Gly Ser Ile Asn Ala Trp Ser
    1175                1180                1185

Thr Lys Glu Pro Phe Ser Trp Ile Lys Val Asp Leu Leu Ala Pro
    1190                1195                1200

Met Ile Ile His Gly Ile Lys Thr Gln Gly Ala Arg Gln Lys Phe
    1205                1210                1215

Ser Ser Leu Tyr Ile Ser Gln Phe Ile Ile Met Tyr Ser Leu Asp
    1220                1225                1230

Gly Lys Lys Trp Gln Thr Tyr Arg Gly Asn Ser Thr Gly Thr Leu
    1235                1240                1245

Met Val Phe Phe Gly Asn Val Asp Ser Ser Gly Ile Lys His Asn
    1250                1255                1260

Ile Phe Asn Pro Pro Ile Ile Ala Arg Tyr Ile Arg Leu His Pro
    1265                1270                1275

Thr His Tyr Ser Ile Arg Ser Thr Leu Arg Met Glu Leu Met Gly
    1280                1285                1290

Cys Asp Leu Asn Ser Cys Ser Met Pro Leu Gly Met Glu Ser Lys
    1295                1300                1305

Ala Ile Ser Asp Ala Gln Ile Thr Ala Ser Ser Tyr Phe Thr Asn
    1310                1315                1320

Met Phe Ala Thr Trp Ser Pro Ser Lys Ala Arg Leu His Leu Gln
    1325                1330                1335

Gly Arg Ser Asn Ala Trp Arg Pro Gln Val Asn Asn Pro Lys Glu
    1340                1345                1350

Trp Leu Gln Val Asp Phe Gln Lys Thr Met Lys Val Thr Gly Val
    1355                1360                1365

Thr Thr Gln Gly Val Lys Ser Leu Leu Thr Ser Met Tyr Val Lys
    1370                1375                1380

Glu Phe Leu Ile Ser Ser Ser Gln Asp Gly His Gln Trp Thr Leu
    1385                1390                1395

Phe Phe Gln Asn Gly Lys Val Lys Val Phe Gln Gly Asn Gln Asp
    1400                1405                1410

Ser Phe Thr Pro Val Val Asn Ser Leu Asp Pro Pro Leu Leu Thr
    1415                1420                1425

Arg Tyr Leu Arg Ile His Pro Gln Ser Trp Val His Gln Ile Ala
    1430                1435                1440

Leu Arg Met Glu Val Leu Gly Cys Glu Ala Gln Asp Leu Tyr
    1445                1450                1455

<210> SEQ ID NO 4
<211> LENGTH: 1438
<212> TYPE: PRT
<213> ORGANISM: Artificial Sequence
<220> FEATURE:
<223> OTHER INFORMATION: Derived from human FVIII sequence

<400> SEQUENCE: 4
```

-continued

```
Ala Thr Arg Arg Tyr Tyr Leu Gly Ala Val Glu Leu Ser Trp Asp Tyr
  1               5                  10                  15

Met Gln Ser Asp Leu Gly Glu Leu Pro Val Asp Ala Arg Phe Pro Pro
             20                  25                  30

Arg Val Pro Lys Ser Phe Pro Phe Asn Thr Ser Val Val Tyr Lys Lys
         35                  40                  45

Thr Leu Phe Val Glu Phe Thr Asp His Leu Phe Asn Ile Ala Lys Pro
     50                  55                  60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
             100                 105                 110

Glu Tyr Asp Asp Gln Thr Ser Gln Arg Glu Lys Glu Asp Asp Lys Val
         115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
```

```
            420                 425                 430
Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
            450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                    485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
            530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                    565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                    645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
            690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                    725                 730                 735

Ile Glu Pro Arg Ser Phe Ser Gln Asn Pro Pro Val Leu Lys Arg His
                740                 745                 750

Gln Arg Glu Ile Thr Arg Thr Thr Leu Gln Ser Asp Gln Glu Glu Ile
            755                 760                 765

Asp Tyr Asp Asp Thr Ile Ser Val Glu Met Lys Lys Glu Asp Phe Asp
            770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                    805                 810                 815

Met Ser Ser Ser Pro His Val Leu Arg Asn Arg Ala Gln Ser Gly Ser
                820                 825                 830

Val Pro Gln Phe Lys Lys Val Val Phe Gln Glu Phe Thr Asp Gly Ser
            835                 840                 845
```

```
Phe Thr Gln Pro Leu Tyr Arg Gly Glu Leu Asn Glu His Leu Gly Leu
    850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
                900                 905                 910

Val Lys Pro Asn Glu Thr Lys Thr Tyr Phe Trp Lys Val Gln His His
            915                 920                 925

Met Ala Pro Thr Lys Asp Glu Phe Asp Cys Lys Ala Trp Ala Tyr Phe
        930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
            980                 985                 990

Lys Ser Trp Tyr Phe Thr Glu Asn Met Glu Arg Asn Cys Arg Ala Pro
        995                 1000                1005

Cys Asn Ile Gln Met Glu Asp Pro Thr Phe Lys Glu Asn Tyr Arg
    1010                1015                1020

Phe His Ala Ile Asn Gly Tyr Ile Met Asp Thr Leu Pro Gly Leu
    1025                1030                1035

Val Met Ala Gln Asp Gln Arg Ile Arg Trp Tyr Leu Leu Ser Met
    1040                1045                1050

Gly Ser Asn Glu Asn Ile His Ser Ile His Phe Ser Gly His Val
    1055                1060                1065

Phe Thr Val Arg Lys Lys Glu Glu Tyr Lys Met Ala Leu Tyr Asn
    1070                1075                1080

Leu Tyr Pro Gly Val Phe Glu Thr Val Glu Met Leu Pro Ser Lys
    1085                1090                1095

Ala Gly Ile Trp Arg Val Glu Cys Leu Ile Gly Glu His Leu His
    1100                1105                1110

Ala Gly Met Ser Thr Leu Phe Leu Val Tyr Ser Asn Lys Cys Gln
    1115                1120                1125

Thr Pro Leu Gly Met Ala Ser Gly His Ile Arg Asp Phe Gln Ile
    1130                1135                1140

Thr Ala Ser Gly Gln Tyr Gly Gln Trp Ala Pro Lys Leu Ala Arg
    1145                1150                1155

Leu His Tyr Ser Gly Ser Ile Asn Ala Trp Ser Thr Lys Glu Pro
    1160                1165                1170

Phe Ser Trp Ile Lys Val Asp Leu Leu Ala Pro Met Ile Ile His
    1175                1180                1185

Gly Ile Lys Thr Gln Gly Ala Arg Gln Lys Phe Ser Ser Leu Tyr
    1190                1195                1200

Ile Ser Gln Phe Ile Ile Met Tyr Ser Leu Asp Gly Lys Lys Trp
    1205                1210                1215

Gln Thr Tyr Arg Gly Asn Ser Thr Gly Thr Leu Met Val Phe Phe
    1220                1225                1230

Gly Asn Val Asp Ser Ser Gly Ile Lys His Asn Ile Phe Asn Pro
    1235                1240                1245
```

```
Pro Ile Ile Ala Arg Tyr Ile Arg Leu His Pro Thr His Tyr Ser
    1250                1255                1260

Ile Arg Ser Thr Leu Arg Met Glu Leu Met Gly Cys Asp Leu Asn
1265                1270                1275

Ser Cys Ser Met Pro Leu Gly Met Glu Ser Lys Ala Ile Ser Asp
    1280                1285                1290

Ala Gln Ile Thr Ala Ser Ser Tyr Phe Thr Asn Met Phe Ala Thr
    1295                1300                1305

Trp Ser Pro Ser Lys Ala Arg Leu His Leu Gln Gly Arg Ser Asn
    1310                1315                1320

Ala Trp Arg Pro Gln Val Asn Asn Pro Lys Glu Trp Leu Gln Val
    1325                1330                1335

Asp Phe Gln Lys Thr Met Lys Val Thr Gly Val Thr Thr Gln Gly
    1340                1345                1350

Val Lys Ser Leu Leu Thr Ser Met Tyr Val Lys Glu Phe Leu Ile
    1355                1360                1365

Ser Ser Ser Gln Asp Gly His Gln Trp Thr Leu Phe Phe Gln Asn
    1370                1375                1380

Gly Lys Val Lys Val Phe Gln Gly Asn Gln Asp Ser Phe Thr Pro
    1385                1390                1395

Val Val Asn Ser Leu Asp Pro Pro Leu Leu Thr Arg Tyr Leu Arg
    1400                1405                1410

Ile His Pro Gln Ser Trp Val His Gln Ile Ala Leu Arg Met Glu
    1415                1420                1425

Val Leu Gly Cys Glu Ala Gln Asp Leu Tyr
    1430                1435

<210> SEQ ID NO 5
<211> LENGTH: 10
<212> TYPE: PRT
<213> ORGANISM: Artificial Sequence
<220> FEATURE:
<223> OTHER INFORMATION: Cyclic RGD peptide
<220> FEATURE:
<221> NAME/KEY: RGD peptideCyclic
<222> LOCATION: (2)..(2)
<223> OTHER INFORMATION: X is penicillamine

<400> SEQUENCE: 5

Gly Xaa Gly Arg Gly Asp Ser Pro Cys Ala
1               5                   10

<210> SEQ ID NO 6
<211> LENGTH: 5
<212> TYPE: PRT
<213> ORGANISM: Artificial Sequence
<220> FEATURE:
<223> OTHER INFORMATION: Synthetic

<400> SEQUENCE: 6

Ser Phe Ser Gln Asn
1               5

<210> SEQ ID NO 7
<211> LENGTH: 12
<212> TYPE: PRT
<213> ORGANISM: Artificial Sequence
```

```
<220> FEATURE:
<223> OTHER INFORMATION: Synthetic

<400> SEQUENCE: 7

Ser Gln Asn Pro Pro Val Leu Lys Arg His Gln Arg
1               5                   10
```